US012649840B2

(12) United States Patent
Zabula et al.

(10) Patent No.: US 12,649,840 B2
(45) Date of Patent: Jun. 9, 2026

(54) PROCESSES FOR PRODUCING CYCLIC OLEFINS FROM POLYMERS AND RE-POLYMERIZATION THEREOF

(71) Applicant: ExxonMobil Chemical Patents Inc., Baytown, TX (US)

(72) Inventors: Alexander V. Zabula, Seabrook, TX (US); Lubin Luo, Houston, TX (US); Carlos R. Lopez-Barron, Houston, TX (US); Brian J. Rohde, Houston, TX (US); Mark K. Davis, Humble, TX (US); Frank N. Raushel, Baytown, TX (US); Yong Yang, Kingwood, TX (US); Alan A. Galuska, Ellijay, GA (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 719 days.

(21) Appl. No.: 17/999,232

(22) PCT Filed: May 21, 2021

(86) PCT No.: PCT/US2021/033669

§ 371 (c)(1),
(2) Date: Nov. 18, 2022

(87) PCT Pub. No.: WO2021/242636

PCT Pub. Date: Dec. 2, 2021

(65) Prior Publication Data

US 2023/0220179 A1 Jul. 13, 2023

Related U.S. Application Data

(60) Provisional application No. 63/032,157, filed on May 29, 2020.

(51) Int. Cl.
*C08G 61/08* (2006.01)
*C07C 4/22* (2006.01)
*C08J 11/16* (2006.01)

(52) U.S. Cl.
CPC ................ *C08J 11/16* (2013.01); *C07C 4/22* (2013.01); *C08G 61/08* (2013.01); *C07C 2531/24* (2013.01); *C08G 2261/11* (2013.01); *C08G 2261/122* (2013.01); *C08G 2261/216* (2013.01); *C08G 2261/3321* (2013.01); *C08G 2261/3325* (2013.01); *C08G 2261/418* (2013.01); *C08J 2319/00* (2013.01); *C08J 2365/00* (2013.01)

(58) Field of Classification Search
USPC .......................................................... 521/40
See application file for complete search history.

(56) References Cited

U.S. PATENT DOCUMENTS

| | | | | |
|---|---|---|---|---|
| 4,988,764 | A | 1/1991 | Nishio et al. | 525/66 |
| 5,312,940 | A | 5/1994 | Grubbs et al. | 556/136 |
| 5,342,909 | A | 8/1994 | Grubbs et al. | 526/171 |
| 5,656,693 | A | 8/1997 | Ellul et al. | 525/171 |
| 5,831,108 | A | 11/1998 | Grubbs et al. | 556/21 |
| 5,969,170 | A | 10/1999 | Grubbs et al. | 556/21 |
| 6,111,121 | A | 8/2000 | Grubbs et al. | 556/21 |
| 6,225,432 | B1 | 5/2001 | Weng et al. | 526/351 |
| 6,759,537 | B2 | 7/2004 | Grubbs et al. | 548/101 |
| 6,803,429 | B2 | 10/2004 | Morgan et al. | 526/135 |
| 6,921,735 | B2 | 7/2005 | Hoveyda et al. | 502/152 |
| 7,312,331 | B2 | 12/2007 | Bertrand et al. | 546/2 |
| 7,329,758 | B1 | 2/2008 | Grubbs et al. | 548/103 |
| 8,063,232 | B2 | 11/2011 | Hagadorn et al. | 548/402 |
| 8,283,419 | B2 | 10/2012 | Hagadorn et al. | 525/245 |
| 8,329,921 | B2 | 12/2012 | Hagadorn et al. | 548/402 |
| 8,372,930 | B2 | 2/2013 | Brant et al. | 526/351 |
| 8,399,725 | B2 | 3/2013 | Brant et al. | 585/416 |
| 8,519,147 | B2 | 8/2013 | Hagadorn et al. | 548/103 |
| 8,524,930 | B2 | 9/2013 | Holtcamp et al. | 556/20 |
| 8,557,902 | B2 | 10/2013 | Holtcamp et al. | 524/313 |
| 8,604,148 | B2 | 12/2013 | Holtcamp et al. | 526/281 |
| 8,623,962 | B2 | 1/2014 | Hagadorn et al. | 525/245 |
| 8,809,563 | B2 | 8/2014 | Holtcamp et al. | 556/22 |
| 9,024,034 | B2 | 5/2015 | Holtcamp et al. | C07F 15/0046 |
| 9,181,360 | B2 | 11/2015 | Holtcamp et al. | C08F 4/80 |
| 9,714,393 | B2 | 7/2017 | Ng et al. | C10G 75/04 |
| 10,093,864 | B2 | 10/2018 | Tandon | C10G 1/10 |

(Continued)

FOREIGN PATENT DOCUMENTS

| | | | |
|---|---|---|---|
| EP | 1693357 | 8/2006 | C07C 6/06 |
| WO | WO1998/040373 | 9/1998 | C07D 307/93 |
| WO | WO2018/232212 | 12/2018 | C08G 61/06 |

OTHER PUBLICATIONS

William J. Neary and Justin G. Kennemur; ACS Macro Letters 2019 8 (1), 46-56; DOI: 10.1021/acsmacrolett.8b00885 (Year: 2019).*
Liu, Peng, and Chunjin Ai. "Olefin metathesis reaction in rubber chemistry and industry and beyond." Industrial & Engineering Chemistry Research 57.11 (2018): 3807-3820. (Year: 2018).*
*Chemical and Engineering News*, v.63(5), p. 27 (1985).
Alder, R. W. (1996) "Bis(diisopropylamino)carbene," *Angew. Chem. Int. Ed.*, v.35(10), pp. 1121-1123.
Amin, S. B. et al. (2008) "Versatile Pathways for in-situ Polyolefin Functionalization with Heteroatoms: Catalytic Chain Transfer," *Angew. Chem. Int. Ed.*, v.47(11), pp. 2006-2025.

(Continued)

*Primary Examiner* — Terressa Boykin
(74) *Attorney, Agent, or Firm* — Kevin Davis; WOMBLE BOND DICKINSON (US) LLP

(57) ABSTRACT

In some embodiments, a process for producing a cyclic olefin includes introducing a polymer to a metathesis catalyst in a reaction vessel under reaction conditions. The process includes obtaining a cyclic olefin product comprising the cyclic olefin. In some embodiments, a process for producing a cyclic olefin includes introducing an article comprising a polymer to a metathesis catalyst in a reaction vessel under reaction conditions. The process includes obtaining a cyclic olefin product comprising the cyclic olefin.

10 Claims, 2 Drawing Sheets

(56) References Cited

U.S. PATENT DOCUMENTS

| | | | | |
|---|---|---|---|---|
| 10,494,490 | B2 | 12/2019 | Xiong et al. | C08J 3/22 |
| 10,519,301 | B2 | 12/2019 | Bohm | C08L 9/00 |
| 2002/0015519 | A1 | 2/2002 | Tokas et al. | 382/147 |
| 2002/0053379 | A1 | 5/2002 | Tokas et al. | 152/209.6 |
| 2002/0166629 | A1 | 11/2002 | Caster et al. | 156/309.3 |
| 2003/0058812 | A1 | 3/2003 | Kendall et al. | 370/322 |
| 2003/0069374 | A1 | 4/2003 | Grubbs et al. | 526/171 |
| 2003/0149274 | A1 | 8/2003 | Herrmann et al. | 548/101 |
| 2003/0186035 | A1 | 10/2003 | Cruce et al. | 428/292.4 |
| 2003/0230598 | A1 | 12/2003 | Kendall et al. | 222/145.6 |
| 2005/0261451 | A1 | 11/2005 | Ung et al. | 526/171 |
| 2006/0052487 | A1 | 3/2006 | Cruce et al. | 524/2 |
| 2008/0064891 | A1 | 3/2008 | Lee | 554/124 |
| 2009/0076226 | A1 | 3/2009 | Meca et al. | 525/340 |
| 2009/0306268 | A1 | 12/2009 | Pawlow et al. | 524/435 |
| 2010/0010161 | A1 | 1/2010 | Arriola et al. | 525/192 |
| 2010/0069573 | A1 | 3/2010 | Arriola et al. | 525/209 |
| 2010/0113719 | A1 | 5/2010 | Patton et al. | 526/134 |
| 2010/0168352 | A1 | 7/2010 | Arriola et al. | 526/171 |
| 2010/0222513 | A1 | 9/2010 | Arriola et al. | 525/195 |
| 2010/0324094 | A1 | 12/2010 | Tillekeratne et al. | 514/337 |
| 2011/0112349 | A1 | 5/2011 | Holtcamp et al. | 585/639 |
| 2012/0077945 | A1 | 3/2012 | Holtcamp et al. | 526/171 |
| 2014/0099573 | A1 | 4/2014 | Weitekamp et al. | 430/18 |
| 2015/0118188 | A1 | 4/2015 | Weitekamp et al. | G03F 7/20 |
| 2016/0215089 | A1 | 7/2016 | Tuba et al. | G08G 61/08 |
| 2017/0121242 | A1 | 5/2017 | Iaccino et al. | C07C 5/373 |
| 2017/0121243 | A1 | 5/2017 | Iaccino et al. | C07C 5/373 |
| 2017/0121244 | A1 | 5/2017 | Iaccino et al. | C07C 5/373 |
| 2017/0121245 | A1 | 5/2017 | Iaccino et al. | C07C 5/373 |
| 2017/0121246 | A1 | 5/2017 | Iaccino et al. | C07C 5/373 |
| 2017/0121247 | A1 | 5/2017 | Iaccino et al. | C07C 5/373 |
| 2017/0121248 | A1 | 5/2017 | Iaccino et al. | C07C 5/373 |
| 2017/0121252 | A1 | 5/2017 | Iaccino et al. | C07C 5/373 |
| 2017/0121254 | A1 | 5/2017 | Iaccino et al. | C07C 5/373 |
| 2017/0121255 | A1 | 5/2017 | Iaccino | C07C 5/373 |
| 2017/0190806 | A1 | 7/2017 | Obrecht et al. | C08C 19/28 |
| 2018/0067393 | A1 | 3/2018 | Weitekamp | G03F 7/029 |
| 2018/0127539 | A1 | 5/2018 | Tuba et al. | C08G 61/08 |
| 2018/0265607 | A1 | 9/2018 | Kennemur et al. | C08F 12/30 |
| 2018/0319721 | A1 | 11/2018 | Sangar et al. | |

OTHER PUBLICATIONS

Bertrand, G. and Bourissou, D. et al. (2000) "Stable Carbenes," *Chem. Rev.*, v.100(1), pp. 39-92.

Bertrand, G. and Lavallo, V. et al. (2005) "A Rigid Cyclic (Alkyl)(amino)carbene Ligand Leads to Isolation of Low-Coordinate Transition-Metal Complexes," *Angew. Chem. Int. Ed.*, v.44(44), pp. 7236-7239.

Chung, T. C. (2002) "Synthesis of Functional Polyolefin Copolymers with Graft and Block Structures," *Prog. Polym. Sci.*, v.27(1), pp. 39-85.

Dragutan, V. et.al. (2010) "A Selective Route for Synthesis of Linear Polydicyclopentadien," *Green Metathesis Chemistry: Great Challenges in Synthesis, Catalysis, and Nanotechnology*, pp. 369-380.

Enders, D. et al. (1995) "Preparation, Structure, and Reactivity of 1,3,4-Triphenyl-4,5-dihydro-1H-1,2,4-triazol-5-ylidene, a New Stable Carbene," *Angewandte Chemical Int. Ed.*, v.34(9), pp. 1021-1023.

Engel, J. and Jensen, V. et al. (2017) "Loss and Reformation of Ruthenium Alkylidene: Connecting Olefin Metathesis, Catalyst Deactivation, Regeneration, and Isomerization," *J. Am. Chem. Soc.*, v.139(46), pp. 16609-16619.

Feist, J. D. et al. (2020) "Enol Ethers Are Effective Monomers for Ring-Opening Metathesis Polymerization: Synthesis of Degradable and Depolymerizable Poly(2,3-dihydrofuran)" *J. Am. Chem. Soc.* 2020, v.142(3), pp. 1186-1189.

Fogg, D. E. and Higman, C. S. et al. (2016) "Catalyst Decomposition During Olefin Metathesis Yields Isomerization-Active Ruthenium Nanoparticles," *ChemCatChem*, v.8(15), pp. 2446-2449.

Sytniczuk, A. and Grela, K. et al. (2018) "Sequential Alkene Isomerization and Ring-Closing Metathesis in Production of Macrocyclic Musks from Biomass," *Chem. Eur. J*,. v.24(41), pp. 10403-104087.

Hermann, W. A. et al. (1996) "N-Heterocyclic Carbenest: Generation under Mild Conditions and Formation of Group 8-10 Transition Metal Complexes Relevant to Catalysis," *Chemistry Eur. J.*, v.2(7), pp. 772-780.

Hermann, W. A. et al. (1996) "Heterocyclic Carbenes:† A High-Yielding Synthesis of Novel, Functionalized N-Heterocyclic Carbenes in Liquid Ammonia," *Chemistry Eur. J.*, v.2(12), pp. 1627-1636.

Lopez, R. G. et al. (2007) "Synthesis of Well-Defined Polymer Architectures by Successive Catalytic Olefin Polymerization and Living/Controlled Polymerization Reactions," *Prog. Polym. Sci.*, v.32(4), pp. 419-454.

Mathers, R. T. et al. (2004) "Cross Metathesis Functionalization of Polyolefin," *Chem. Commun.*, pp. 422-423.

Mulhearn, W. D. and Register, R. A. (2017) "Synthesis of Narrow-Distribution, High-Molecular-Weight ROMP Polycyclopentene via Suppression of Acyclic Metathesis Side Reactions," *ACS Macro Letters*, v.6(2), pp. 112-116.

Tuba, R. et al. (2016) "Synthesis of Recyclable Tire Additives via Equilibrium Ring-Opening Metathesis Polymerization" *ACS Sustainable Chemistry & Engineering*, v.4(11), pp. 6090-6094.

Zabula, A. V. et al. (2008) "Mono- and Bidentate Benzannulated N-Heterocyclic Germylenes, Stannylenes and Plumbylenes," *Eur. J. Inorg. Chem.*, v.2008(33) pp. 5165-5179.

* cited by examiner $^1H$ NMR SPECTRUM FOR RECYCLED CYCLOPENTENE ($CDCl_3$)

PROCESSES FOR PRODUCING CYCLIC OLEFINS FROM POLYMERS AND RE-POLYMERIZATION THEREOF

CROSS REFERENCE TO RELATED APPLICATIONS

This application is a National Phase Application claiming priority to PCT Application Serial No. PCT/US2021/033669 filed 21 May 2021, which claims the benefit of and priority to U.S. Provisional Application No. 63/032,157 filed May 29, 2020, the disclosure of U.S. Provisional Application No. 63/032,157 is incorporated herein by reference.

FIELD

The present disclosure relates to processes for producing cyclic olefins from polymers and re-polymerization of such recycled cyclic olefins.

BACKGROUND

Rubber compounds used in vehicle tires are composite materials that include polymers, such as natural rubber or synthetic rubbers that have been blended with reinforcing fillers, such as carbon black or silica, as well as with a variety of additives such as sulfur. The tire is assembled from a multitude of extruded or calendered components into the basic circular shape and is then molded and vulcanized (e.g., cured) in a tire press. For example, curing generally includes incorporating in the tire compounds a mixture of curing agents including an accelerator, sulfur, and accelerator activating compounds, such as stearic acid and zinc oxide, to facilitate the forming of sulfur cross-links upon applying heat to the rubber. Vulcanization results in the creation of a three dimensional network of sulfur cross-links within the rubber phase which link the various polymer chains to form a composite which cannot be reshaped once it has been formed and cured. As a result, the recycling and reuse of vulcanized rubber products, such as worn tires, is difficult because the vulcanized rubber cannot be reshaped or simply reconstituted by dissolving it in a solvent in order to form the vulcanized rubber into a new shape.

Because of the ever increasing cost of oil derived raw materials, such as synthetic rubbers and carbon black fillers, there is considerable interest in the reuse of products such as worn vulcanized rubber tires made from these materials. Millions of used tires and other rubber products are discarded annually and only a minor fraction of them are being recycled into new products. The small amounts that are reused are usually first broken up to remove the non-rubber components of the tire, such as steel cords, beads, etc., and the remaining rubber compound is ground-up into particles of different sizes for use in a wide variety of applications, such as synthetic turf for football, soccer, and other sport related playing surfaces. Additional applications of these ground-up vulcanized rubber particles include use of the products in molded or extruded materials such as floor mats, etc. Reuse of such recycled rubber products in high performance products such as tires is limited to exceedingly small quantities because the ground rubber particles typically adversely affect key properties for the performance of the tire.

Prior rubber recycling processes include first devulcanizing the previously cured and to be recycled rubber, prior to mixing the vulcanized ground rubber with fresh rubber to compound and recurring/reprocessing. Although many different processes of devulcanization exist, the processes generally include first grinding the recycled vulcanized rubber to a suitable size and then employing a process to reduce the concentration of sulfur cross-links in the recycled rubber prior to mixing the recycled rubber with fresh rubber compound and ultimately curing the essentially devulcanized mixture. Although such processes can be effective in avoiding some of the potential issues with utilizing recycled rubber, the processes are generally complex, add significant time and cost to the rubber product manufacturing process, and often result in significant and undesirable structural changes to the rubber molecules. In addition, while the use of untreated recycled rubber for high performance product applications is generally limited to about 1-2%, the use of partially devulcanized recycled rubber may only be slightly higher due to current limitations of the devulcanization process. Most of these adverse effects result because the vulcanized ground rubber particles do not dissolve in the fresh rubber compound on a molecular scale, but instead stay intact and often act as defects once the product is processed by molding and vulcanization of the new composition.

There is a need for new processes for recycling vulcanized rubber.

Relevant background information may be found in the following: Mathers, R. T. et al. (2004) "Cross Metathesis Functionalization of Polyolefin," *Chem. Commun.*, pp. pp. 422-423; Amin, S. B. et al. (2008) "Versatile Pathways for In-Situ Polyolefin Functionalization with Heteroatoms: Catalytic Chain Transfer,"*Angew. Chem. Int. Ed.*, v. 47, pp. 2006-2025; T. C. Chung (2002) "Synthesis of Functional Polyolefin Copolymers with Graft and Block Structures," *Prog. Polym. Sci.*, v. 27(1), pp. 39-85; Lopez, R. G. et al. (2007) "Synthesis of Well-Defined Polymer Architectures by Successive Catalytic Olefin Polymerization and Living/Controlled Polymerization Reactions," *Prog. Polym. Sci.*, v. 32(4), pp. 419-454; U.S. Pat. Nos. 8,283,419; 6,803,429; US 2008/0064891; WO 1998/040373; U.S. Pat. Nos. 4,988,764; 6,225,432; EP 1 693 357; U.S. Pat. Nos. 8,399,725; 8,372,930; 10,519,301; 10,494,490; 10,093,864; US 2018/0127539; US 2016/0215089; US 2003/0230598; US 2003/0058812; US 2002/0166629; US 2002/0053379; US 2002/0015519; US 2018/0265607; US 2018/0067393; US 2017/0190806; US 2015/0118188; US 2014/0099573; US 2010/0324094; US 2010/0113719; US 2009/0076226; US 2006/0052487; US 2003/0186035; US 2003/0069374; US 2010/0222513; US 2010/0168352; US 2010/0069573; US 2010/0010161; US 2003/0149274; US 2018/0265607; US 2017/0190806; US 2009/0306268; US 2018/0319721; US 2017/0121255; US 2017/0121254; US 2017/0121252; US 2017/0121248; US 2017/0121247; US 2017/0121246; US 2017/0121245 US 2017/0121244; US 2017/0121243; US 2017/0121242; WO2018/232212; U.S. Pat. Nos. 8,329,921; 8,519,147; US 2011/0112349; U.S. Pat. Nos. 8,809,563; 9,024,034; 8,557,902; US 2012/0077945; U.S. Pat. Nos. 8,524,930; 9,181,360; 8,623,962; 8,063,232; 8,604,148; 9,714,393; Feist, J. D. et al. (2020) "Enol Ethers Are Effective Monomers for Ring-Opening Metathesis Polymerization: Synthesis of Degradable and Depolymerizable Poly(2,3-dihydrofuran)" *J. Am. Chem. Soc.* 2020, v. 142(3), pp. 1186-1189; Tuba, R. et al. (2016) "Synthesis of Recyclable Tire Additives via Equilibrium Ring-Opening Metathesis Polymerization" *ACS Sustainable Chemistry & Engineering*, v. 4(11), pp. 6090-6094; Mulhearn, W. D. et al. (2017) "Synthesis of Narrow-Distribution, High-Molecular-Weight ROMP Polycyclopentene via Suppression of Acyclic Metathesis Side Reactions," *ACS Macro Letters*, v. 6(2), pp.

112-116; Higman, C. S. et al. (2016) "Catalyst Decomposition during Olefin Metathesis Yields Isomerization-Active Ruthenium Nanoparticles," *ChemCatChem*, v. 8(15), pp. 2446-2449; Engel, J. et al. (2017) "Loss and Reformation of Ruthenium Alkylidene: Connecting Olefin Metathesis, Catalyst Deactivation, Regeneration, and Isomerization," *J. Am. Chem. Soc.*, v. 139(46), pp. 16609-16619; and Sytniczuk, A. et al. (2018) "Sequential Alkene Isomerization and Ring-Closing Metathesis in Production of Macrocyclic Musks from Biomass," *Chem. Eur. J.*, v. 24(41), pp. 10403-10408.

SUMMARY

In some embodiments, a process for producing a cyclic olefin includes introducing a polymer to a metathesis catalyst in a reaction vessel under reaction conditions. The process includes obtaining a product comprising the cyclic olefin.

In some embodiments, a process for producing a cyclic olefin includes introducing an article comprising a polymer to a metathesis catalyst in a reaction vessel under reaction conditions. The process includes obtaining a product comprising the cyclic olefin.

In some embodiments, a process for producing a polymer includes introducing a recycled cyclic olefin to a metathesis catalyst in a reaction vessel under polymerization reaction conditions.

DETAILED DESCRIPTION

Figure 1:
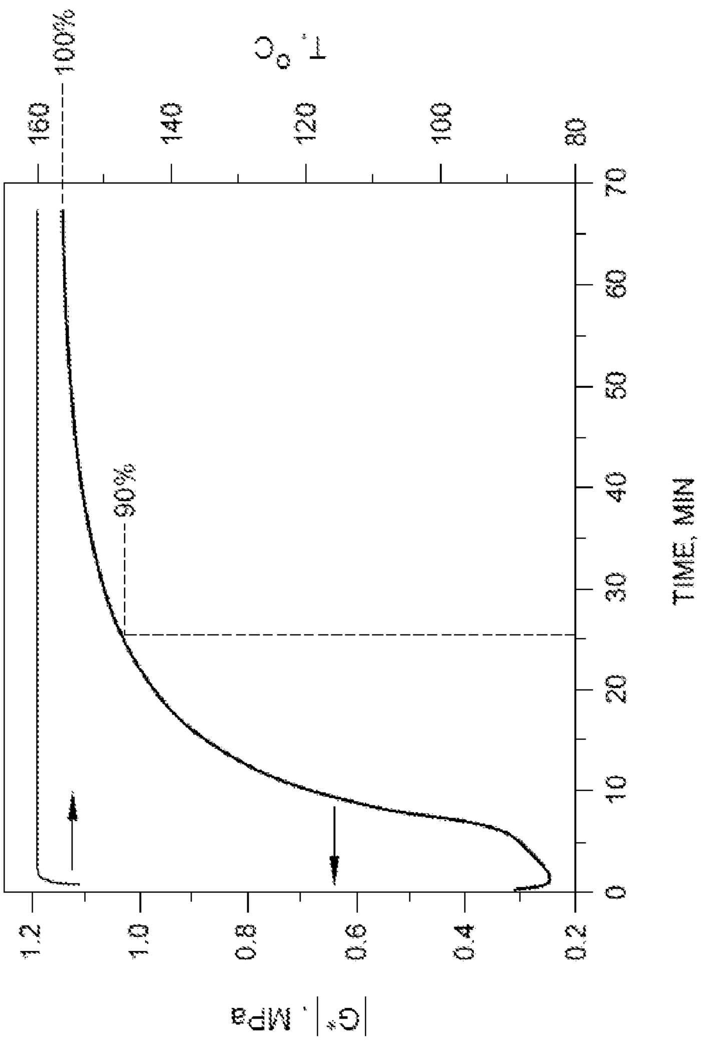
FIG. 1 is a graph illustrating vulcanization (cure kinetics) curve for the CPR sample measured at 160° C., according to an embodiment.

The present disclosure relates to processes for producing cyclic olefins via ring closing metathesis. Processes of the present disclosure can include treating a polymer (such as a polypentenamer or polyoctenamer) with a ring closing metathesis (RCM) catalyst to provide high yields of cyclic olefins (such as cyclopentene or cyclooctene). The high yield also provides high purity of the cyclic olefins. It has been discovered that high yields of cyclic olefins may be obtained without the use of added diluent for the depolymerization, which improves the cost and throughput of an industrial scale depolymerization process. It has been further discovered that high yields of cyclic olefins may be obtained when treating vulcanized rubber (such as tires), for example with little or no pretreatment of the vulcanized rubber. Therefore, recycled cyclic olefins can be obtained in high yield (and high purity) for repurposing as starting monomers for polymerizations. The high purity of the recycled cyclic olefins can provide high purity recycled polymers (and vulcanized products thereof).

The terms "cis" and "(Z)" as used herein are used interchangeably and refers to the cis configuration of carbon-carbon double bonds of a polymer backbone. Cis can refer to a carbon-carbon double bond represented by the structure:

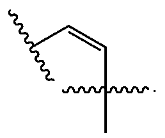

The terms "trans" and "(E)" as used herein are used interchangeably and refers to the trans configuration of carbon-carbon double bonds of a polymer backbone. Trans can refer to a carbon-carbon double bond represented by the structure:

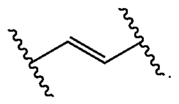 [SMILES: */C=C/*]

As used herein, $M_n$ is number average molecular weight, $M_w$ is weight average molecular weight, and $M_z$ is z average molecular weight, wt % is weight percent, and mol % is mole percent. Molecular weight distribution (MWD), also referred to as polydispersity index (PDI), is the value of $M_w$ divided by $M_n$. Unless otherwise noted, all molecular weight units (e.g., $M_w$, $M_n$, $M_z$) are g/mol.

"Catalyst activity" is a measure of how active the catalyst is and is reported as the grams of product cyclic olefin produced per gram of catalyst (cat) per hour (g-cyclic olefin/g-catalyst/hour). For calculating catalyst activity, also referred to as catalyst productivity, only the weight of the metal component of the catalyst is used. Catalyst activity herein may also be referred to as grams of product cyclic olefin produced per gram of catalyst (cat).

The term "isomerization" refers to a single or multiple rearrangements of carbon bonds without moving carbon atoms in a polymer chain. An example of such transformation includes the migration of the bonds and hydrogen atoms in a $—C(1)H_2—C(2)H_2—C(3)H{=}C(4)H—$ unit to the $—C(1)H{=}C(2)H—C(3)H_2—C(4)H_2—$ fragment.

When reference is made to "recycled rubber" or "ground rubber" within this disclosure, it is to be understood that the term refers to previously vulcanized rubber.

The term "recycled olefin" refers to cyclic monomers obtained upon ring-closing metathesis depolymerization of polyalkenamers.

Cyclic monomers contain less than 1.1 wt % of non-cyclic olefins, typically less 0.1 wt %.

For the purposes of this invention and the claims thereto, the numbering scheme for the Periodic Table Groups is used as described in *Chemical and Engineering News*, v. 63(5), pg. 27 (1985). Therefore, a "group 4 metal" is an element from group 4 of the Periodic Table, e.g. Hf, Ti, or Zr.

An "olefin," alternatively referred to as "alkene," is a linear, branched, or cyclic compound of carbon and hydrogen having at least one double bond. For purposes of this specification and the claims appended thereto, when a polymer or copolymer is referred to as comprising an olefin, the olefin present in such polymer or copolymer is the polymerized form of the olefin. For example, when a copolymer is said to have an "ethylene" content of 35 wt % to 55 wt %, it is understood that the mer unit in the copolymer is derived from ethylene in the polymerization reaction and said derived units are present at 35 wt % to 55 wt %, based upon the weight of the copolymer. A "polymer" has two or more of the same or different mer units. A "homopolymer" is a polymer having mer units that are the same. A "copolymer" is a polymer having two or more mer units that are different from each other. A "terpolymer" is a polymer having three mer units that are different from each other. Accordingly, the definition of copolymer, as used herein, includes terpolymers and the like. "Different" as used to refer to mer units indicates that the mer units differ from each other by at least one atom or are different isomerically. An "ethylene polymer" or "ethylene copolymer" is a polymer or copolymer comprising at least 50 mole % ethylene derived units, a "propylene polymer" or "propylene copolymer" is a polymer or copolymer comprising at least 50 mole % propylene derived units, and so on.

The term "alpha-olefin" refers to an olefin having a terminal carbon-to-carbon double bond in the structure thereof $R^1R^2C{=}CH_2$, where $R^1$ and $R^2$ can be independently hydrogen or any hydrocarbyl group; preferably $R^1$ is hydrogen and $R^2$ is an alkyl group). A "linear alpha-olefin" is an alpha-olefin defined in this paragraph wherein $R^1$ is hydrogen, and $R^2$ is hydrogen or a linear alkyl group.

For the purposes of the present disclosure, ethylene shall be considered an α-olefin.

As used herein, and unless otherwise specified, the term "$C_n$" means hydrocarbon(s) having n carbon atom(s) per molecule, wherein n is a positive integer.

The term "hydrocarbon" means a class of compounds containing hydrogen bound to carbon, and encompasses (i) saturated hydrocarbon compounds, (ii) unsaturated hydrocarbon compounds, and (iii) mixtures of hydrocarbon compounds (saturated and/or unsaturated), including mixtures of hydrocarbon compounds having different values of n. Likewise, a "$C_m$-$C_y$" group or compound refers to a group or compound comprising carbon atoms at a total number thereof in the range from m to y. Thus, a $C_1$-$C_{50}$ alkyl group refers to an alkyl group comprising carbon atoms at a total number thereof in the range from 1 to 50.

The terms "group," "radical," and "substituent" may be used interchangeably.

The terms "hydrocarbyl radical," "hydrocarbyl group," or "hydrocarbyl" may be used interchangeably and are defined to mean a group consisting of hydrogen and carbon atoms only. Example hydrocarbyls are $C_1$-$C_{100}$ radicals that may be linear, branched, or cyclic, and when cyclic, aromatic or non-aromatic. Examples of such radicals include, but are not limited to, alkyl groups such as methyl, ethyl, n-propyl, isopropyl, n-butyl, isobutyl, sec-butyl, tert-butyl, pentyl, iso-amyl, hexyl, octyl cyclopropyl, cyclobutyl, cyclopentyl, cyclohexyl, cyclooctyl, and the like, aryl groups, such as phenyl, benzyl, naphthyl, and the like.

Unless otherwise indicated, (e.g., the definition of "substituted hydrocarbyl", etc.), the term "substituted" means that at least one hydrogen atom has been replaced with at least one non-hydrogen group, such as a hydrocarbyl group, a heteroatom, or a heteroatom containing group, such as halogen (such as Br, Cl, F or I) or at least one functional group such as $-NR^*_2$, $-OR^*$, $-SeR^*$, $-TeR^*$, $-PR^*_2$, $-AsR^*_2$, $-SbR^*_2$, $-SR^*$, $-BR^*_2$, $-SiR^*_3$, $-GeR^*_3$, $-SnR^*_3$, $-PbR^*_3$, $-(CH_2)q$-$SiR^*_3$, and the like, where q is 1 to 10 and each R* is independently hydrogen, a hydrocarbyl or halocarbyl radical, and two or more R* may join together to form a substituted or unsubstituted completely saturated, partially unsaturated, or aromatic cyclic or polycyclic ring structure), or where at least one heteroatom has been inserted within a hydrocarbyl ring.

The term "substituted hydrocarbyl" means a hydrocarbyl radical in which at least one hydrogen atom of the hydrocarbyl radical has been substituted with at least one heteroatom (such as halogen, e.g., Br, Cl, F or I) or heteroatom-containing group (such as a functional group, e.g., $-NR^*_2$, $-OR^*$, $-SeR^*$, $-TeR^*$, $-PR^*_2$, $-AsR^*_2$, $-SbR^*_2$, $-SR^*$, $-BR^*_2$, $-SiR^*_3$, $-GeR^*_3$, $-SnR^*_3$, $-PbR^*_3$, $-(CH_2)q$-$SiR^*_3$, and the like, where q is 1 to 10 and each R* is independently hydrogen, a hydrocarbyl or halocarbyl radical, and two or more R* may join together to form a substituted or unsubstituted completely saturated, partially unsaturated, or aromatic cyclic or polycyclic ring structure), or where at least one heteroatom has been inserted within a hydrocarbyl ring.

The term "substituted aromatic," means an aromatic group having 1 or more hydrogen groups replaced by a hydrocarbyl, substituted hydrocarbyl, heteroatom or heteroatom containing group.

A "halocarbyl" is a halogen substituted hydrocarbyl group.

For purposes of the present disclosure, in relation to catalyst compounds, the term "substituted" means that a hydrogen group has been replaced with a hydrocarbyl group, a heteroatom, or a heteroatom containing group, such as halogen (such as Br, Cl, F or I) or at least one functional group such as $-NR^*_2$, $-OR^*$, $-SeR^*$, $-TeR^*$, $-PR^*_2$, $-AsR^*_2$, $-SbR^*_2$, $-SR^*$, $-BR^*_2$, $-SiR^*_3$, $-GeR^*_3$, $-SnR^*_3$, $-PbR^*_3$, $-(CH_2)q$-$SiR^*_3$, and the like, where q is 1 to 10 and each R* is independently hydrogen, a hydrocarbyl or halocarbyl radical, and two or more R* may join together to form a substituted or unsubstituted completely saturated, partially unsaturated, or aromatic cyclic or polycyclic ring structure), or where at least one heteroatom has been inserted within a hydrocarbyl ring.

The terms "alkoxy" or "alkoxide" and aryloxy or aryloxide mean an alkyl or aryl group bound to an oxygen atom, such as an alkyl ether or aryl ether group/radical connected to an oxygen atom and can include those where the alkyl group is a $C_1$ to $C_{10}$ hydrocarbyl. The alkyl group may be straight chain, branched, or cyclic. The alkyl group may be saturated or unsaturated. Examples of suitable alkoxy and aryloxy radicals can include methoxy, ethoxy, n-propoxy, iso-propoxy, n-butoxy, iso-butoxy, sec-butoxy, tert-butoxy, phenoxyl, and the like.

The terms "alkyl radical," and "alkyl" are used interchangeably throughout this disclosure. For purposes of this disclosure, "alkyl radical" is defined to be $C_1$-$C_{100}$ alkyls, that may be linear, branched, or cyclic. Examples of such radicals can include methyl, ethyl, n-propyl, isopropyl, n-butyl, isobutyl, sec-butyl, tert-butyl, pentyl, iso-amyl, hexyl, octyl cyclopropyl, cyclobutyl, cyclopentyl, cyclohexyl, cyclooctyl, and the like including their substituted analogues. Substituted alkyl radicals are radicals in which at least one hydrogen atom of the alkyl radical has been substituted with at least a non-hydrogen group, such as a hydrocarbyl group, a heteroatom, or a heteroatom containing group, such as halogen (such as Br, Cl, F or I) or at least one functional group such as $-NR^*_2$, $-OR^*$, $-SeR^*$, $-TeR^*$, $-PR^*_2$, $-AsR^*_2$, $-SbR^*_2$, $-SR^*$, $-BR^*_2$, $-SiR^*_3$, $-GeR^*_3$, $-SnR^*_3$, $-PbR^*_3$, $-(CH_2)q$-$SiR^*_3$, and the like, where q is 1 to 10 and each R* is independently hydrogen, a hydrocarbyl or halocarbyl radical, and two or more R* may join together to form a substituted or unsubstituted completely saturated, partially unsaturated, or aromatic cyclic or polycyclic ring structure), or where at least one heteroatom has been inserted within a hydrocarbyl ring.

The term "aryl" or "aryl group" means an aromatic ring (typically made of 6 carbon atoms) and the substituted variants thereof, such as phenyl, 2-methyl-phenyl, xylyl, 4-bromo-xylyl. Likewise, heteroaryl means an aryl group where a ring carbon atom (or two or three ring carbon atoms) has been replaced with a heteroatom, such as N, O, or S. As used herein, the term "aromatic" also refers to pseudoaromatic heterocycles which are heterocyclic substituents that have similar properties and structures (nearly planar) to aromatic heterocyclic ligands, but are not by definition aromatic.

Where isomers of a named alkyl, alkenyl, alkoxide, or aryl group exist (e.g., n-butyl, iso-butyl, sec-butyl, and tert-butyl) reference to one member of the group (e.g., n-butyl) shall expressly disclose the remaining isomers (e.g., iso-butyl, sec-butyl, and tert-butyl) in the family. Likewise, reference to an alkyl, alkenyl, alkoxide, or aryl group without specifying a particular isomer (e.g., butyl) expressly discloses all isomers (e.g., n-butyl, iso-butyl, sec-butyl, and ten-butyl).

The term "independently," when referenced to selection of multiple items from within a given group, means that the selected choice for a first item does not necessarily influence the choice of any second or subsequent item. That is, independent selection of multiple items within a given group means that the individual items may be the same or different from one another.

The following abbreviations may be used herein: Me is methyl, Et is ethyl, Pr is propyl, c-Pr is cyclopropyl, n-Pr is n-propyl, i-Pr is isopropyl, Bu is butyl, n-Bu is normal butyl, i-Bu is isobutyl, s-Bu is sec-butyl, t-Bu is tert-butyl, Oct is octyl, Ph is phenyl, MAO is methylalumoxane, dme is 1,2-dimethoxyethane, p-t-Bu is para-tertiary butyl, TMS is trimethylsilyl, TIBAL is triisobutylaluminum, TNOAL is tri(n-octyl)aluminum, p-Me is para-methyl, Bz and Bn are benzyl (i.e., $CH_2Ph$), THF (also referred to as thf) is tetrahydrofuran, RT is room temperature (and is 23° C. unless otherwise indicated), tol is toluene, EtOAc is ethyl acetate, Cbz is Carbazole, and Cy is cyclohexyl.

In the description herein, the catalyst may be described as a catalyst, a catalyst precursor, a pre-catalyst compound, catalyst compound or a transition metal compound, and these terms are used interchangeably.

An "anionic ligand" is a negatively charged ligand which donates one or more pairs of electrons to a metal ion. A "neutral donor ligand" is a neutrally charged ligand which donates one or more pairs of electrons to a metal ion.

The term "ring atom" means an atom that is part of a cyclic ring structure. By this definition, a benzyl group has six ring atoms and tetrahydrofuran has 5 ring atoms.

A heterocyclic ring is a ring having a heteroatom in the ring structure as opposed to a heteroatom substituted ring where a hydrogen on a ring atom is replaced with a heteroatom. For example, tetrahydrofuran is a heterocyclic ring and N,N-dimethylamino-phenyl is a heteroatom substituted ring.

Polymer Starting Materials

Polymer starting materials can include any suitable polymer (or blend thereof) capable of being depolymerized, for example polymers capable of being depolymerized to form cyclic olefins. Polymers of the present disclosure are typically unsaturated polymers capable of undergoing ring closing metathesis. In at least one embodiment, polymers may include polypentenamer, polyhexenamer, polyheptenamer, or polyoctenamer. Polymers may also include natural rubber, butyl rubber (e.g., sBR), polyisoprene, or polybutadiene rubbers (if isomerization of unsaturated chains occurs in sequential tandem with RCM).

Polymers can be unsaturated polymers that include polyalkenamers, such as a polypentenamer, a polyhexenamer, a polyheptenamer, a polyoctenamer, a polynonenamer, a polydecenamer, a polyundecenamer, a polydodecenamer, a polytridecenamer, a polytetradecenamer, a polypentadecenamer, and copolymers thereof. For example, a polymer can be a cyclopentene-cyclooctene ROMP copolymer ($=CH-(CH_2)_3-CH=CH-(CH_2)_6-CH=$), and depolymerization can provide cyclopentene and cyclooctene products. Polymers formed upon ADMET (acyclic diene metathesis) using linear monomers (such as a linear 1,6-heptadiene and/or a linear 1,9-decadiene) can be depolymerized to form the cyclic monomers (such as cyclopentene and/or cyclooctene). Thus, depolymerization processes of the present disclosure provide new sources of cyclic olefins via polymer intermediates (as starting materials for a depolymerization process). In addition, if cyclic diene starting materials are used to form polymers of the present disclosure, use of diene starting materials such as cyclodecadiene, cyclododecadiene, or cyclotetradecadiene can provide polymer intermediates that upon depolymerization can form high yields of cyclopentene, cyclohexene, and cycloheptene, respectively.

In at least one embodiment, a polymer of the present disclosure has an $M_w$ from about 10,000 g/mol to about 2,000,000 g/mol, such as from about 10,000 g/mol to about 500,000 g/mol, such as from about 15,000 g/mol to about 450,000 g/mol, such as from about 20,000 g/mol to about 400,000 g/mol, such as from about 25,000 g/mol to about 350,000 g/mol, such as from about 30,000 g/mol to about 300,000 g/mol.

In at least one embodiment, a polymer of the present disclosure has an $M_n$ from about 1,000 g/mol to about 1,500,000 g/mol, such as from about 2,000 g/mol to about 300,000 g/mol, such as from about 2,500 g/mol to about 200,000 g/mol, such as from about 5,000 g/mol to about 100,000 g/mol, such as from about 7,500 g/mol to about 75,000 g/mol, such as from about 9,000 g/mol to about 50,000 g/mol.

In at least one embodiment, a polymer of the present disclosure has an $M_z$ from about 10,000 g/mol to about 1,000,000 g/mol, such as from about 15,000 g/mol to about 500,000 g/mol, such as from about 15,000 g/mol to about 450,000 g/mol, such as from about 20,000 g/mol to about 400,000 g/mol, such as from about 25,000 g/mol to about 350,000 g/mol, such as from about 30,000 g/mol to about 300,000 g/mol. Alternatively, a polymer of the present disclosure can have an $M_z$ greater than 500,000 g/mol, such as from about 600,000 g/mol to about 3,000,000 g/mol, such as from about 700,000 g/mol to about 2,500,000 g/mol, such as from about 800,000 g/mol to about 2,000,000 g/mol, such as from about 900,000 g/mol to about 1,500,000 g/mol.

In at least one embodiment, a polymer of the present disclosure has an $M_w/M_n$ (PDI) value from about 1 to about 15, such as about 1 to about 8, such as from about 2 to about 7, such as from about 3 to about 6.5, such as from about 3.5 to about 6, alternatively from about 1.5 to about 2.5.

Furthermore, a polymer of the present disclosure can have a $T_m$ (° C.) of about −50° C. to about 30° C., such as about −45° C. to about −20° C., alternatively about 0° C. to about 30° C.

In at least one embodiment, an unsaturated polymer of the present disclosure is a polypentenamer represented by Formula (I):

(I)

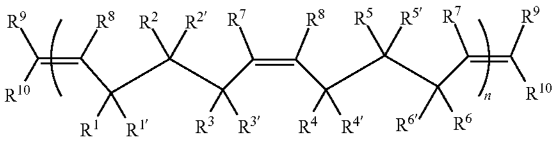

n is a positive integer. In one embodiment, n is from about 1 to about 50,000, such as from about 1,000 to about 10,000, such as from about 5,000 to about 8,000. Each of $R^1$, $R^{1'}$, $R^2$, $R^{2'}$, $R^3$, $R^{3'}$, $R^4$, $R^{4'}$, $R^5$, $R^{5'}$, $R^6$, $R^{6'}$, $R^7$, $R^8$ is independently hydrogen, $C_1$-$C_{40}$ hydrocarbyl, or $R^1$ and $R^3$, $R^1$ and $R^2$, $R^4$ and $R^5$, or $R^4$ and $R^6$ join together to form a saturated or unsaturated cyclic $C_5$-$C_{10}$ hydrocarbyl. In at least one embodiment, each of $R^1$, $R^{1'}$, $R^2$, $R^{2'}$, $R^3$, $R^{3'}$, $R^4$, $R^{4'}$, $R^5$, $R^{5'}$, $R^6$ and $R^{6'}$ is independently hydrogen or $C_1$-$C_{10}$ hydrocarbyl. In at least one embodiment, each of $R^1$, $R^{1'}$, $R^2$, $R^{2'}$, $R^3$, $R^{3'}$, $R^4$, $R^{4'}$, $R^5$, $R^{5'}$, $R^6$ and $R^{6'}$ is hydrogen. $R^7$ and $R^8$ can be hydrogen. $R^9$ and $R^{10}$ are independently hydrogen or an end cap. End caps include ether, amine, aryl, or carboxylic acid. Ether includes ethyl ether, propyl ether, butyl ether, pentyl ether, or hexyl ether.

In at least one embodiment, an unsaturated polymer of the present disclosure is a polyoctenamer represented by Formula (V):

(V)

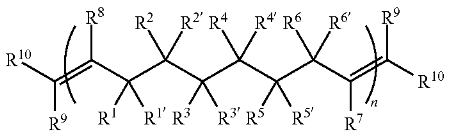

n is a positive integer. In one embodiment, n is from about 1 to about 50,000, such as from about 1,000 to about 10,000, such as from about 5,000 to about 8,000. Each of $R^1$, $R^{1'}$, $R^2$, $R^{2'}$, $R^3$, $R^{3'}$, $R^4$, $R^{4'}$, $R^5$, $R^{5'}$, $R^6$, $R^{6'}$, $R^7$, and $R^8$ is independently hydrogen, $C_1$-$C_{40}$ hydrocarbyl, or $R^1$ and $R^3$, $R^1$ and $R^2$, $R^4$ and $R^5$, or $R^4$ and $R^6$ join together to form a saturated or unsaturated cyclic $C_5$-$C_{10}$ hydrocarbyl. In at least one embodiment, each of $R^1$, $R^{1'}$, $R^2$, $R^{2'}$, $R^3$, $R^{3'}$, $R^4$, $R^{4'}$, $R^5$, $R^{5'}$, $R^6$ and $R^{6'}$ is independently hydrogen or $C_1$-$C_{10}$ hydrocarbyl. In at least one embodiment, each of $R_1$, $R^2$, $R^{2'}$, $R^3$, $R^{3'}$, $R^4$, $R^{4'}$, $R^5$, $R^{5'}$, $R^6$ and $R^{6'}$ is hydrogen. $R^7$ and $R^8$ can be hydrogen. $R^9$ and $R^{10}$ are independently hydrogen or an end cap. End caps include ether, amine, aryl, or carboxylic acid. Ether includes ethyl ether, propyl ether, butyl ether, pentyl ether, or hexyl ether.

In at least one embodiment, an unsaturated polymer of the present disclosure is a polyoctadienamer (polybutadiene) represented by Formula (III):

(III)

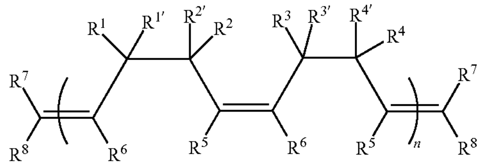

n is a positive integer. In one embodiment, n is from about 1 to about 50,000, such as from about 1,000 to about 10,000, such as from about 5,000 to about 8,000. Each of $R^1$, $R^{1'}$, $R^2$, $R^{2'}$, $R^3$, $R^{3'}$, $R^4$, $R^{4'}$, $R^5$, and $R^6$ is independently hydrogen, $C_1$-$C_{40}$ hydrocarbyl, or $R^1$ and $R^2$, or $R^3$ and $R^4$ join together to form a saturated or unsaturated cyclic $C_5$-$C_{10}$ hydrocarbyl. In at least one embodiment, each of $R^1$, $R^{1'}$, $R^2$, $R^{2'}$, $R^3$, $R^{3'}$, $R^4$, and $R^{4'}$ is independently hydrogen or $C_1$-$C_{10}$ hydrocarbyl. In at least one embodiment, each of $R^1$, $R^{1'}$, $R^2$, $R^{2'}$, $R^3$, $R^{3'}$, $R^4$, and $R^{4'}$ is hydrogen. $R^5$ and $R^6$ can be hydrogen. $R^7$ and $R^8$ are independently hydrogen or an end cap. End caps include ether, amine, aryl, or carboxylic acid. Ether includes ethyl ether, propyl ether, butyl ether, pentyl ether, or hexyl ether.

In at least one embodiment, a polymer is a poly-[cyclopentene]-[cyclooctene] is represented by Formula (IV):

(IV)

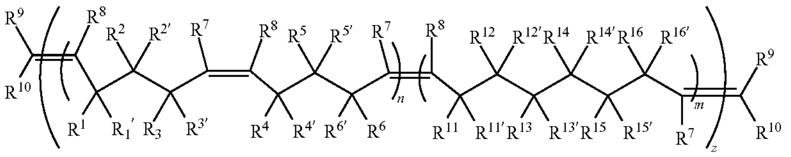

each of n, m, and z is a positive integer. In one embodiment, n is from about 1 to about 25,000, such as from about 500 to about 5,000, such as from about 2,500 to about 4,000. m is from about 1 to about 25,000, such as from about 500 to about 5,000, such as from about 2,500 to about 4,000. z is from about 1 to about 5,000, such as from about 100 to about 3,000, such as from about 300 to about 1,000. Each of $R^1$, $R^{1'}$, $R^2$, $R^{2'}$, $R^3$, $R^{3'}$, $R^4$, $R^{4'}$, $R^5$, $R^{5'}$, $R^6$, $R^{6'}$, $R^7$, $R^8$, $R^{11}$, $R^{11'}$, $R^{12}$, $R^{12'}$, $R^{13}$, $R^{13'}$, $R^{14}$, $R^{14'}$, $R^{15}$, $R^{15'}$, $R^{16}$, and $R^{16'}$ is independently hydrogen, $C_1$-$C_{40}$ hydrocarbyl, or $R^1$ and $R^2$, $R^1$ and $R^3$, $R^2$ and $R^3$, $R^4$ and $R^5$, $R^5$ and $R^6$, $R^{11}$ and $R^{12}$, $R^{12}$ and $R^{13}$, $R^{13}$ and $R^{14}$, $R^{14}$ and $R^{15}$, or $R^{15}$ and $R^{16}$ join together to form a saturated or unsaturated cyclic $C_5$-$C_{10}$ hydrocarbyl. In at least one embodiment, each of $R^1$, $R^{1'}$, $R^2$, $R^{2'}$, $R^3$, $R^{3'}$, $R^4$, $R^{4'}$, $R^5$, $R^{5'}$, $R^6$, $R^{6'}$, $R^7$, $R^8$, $R^{11}$, $R^{11'}$, $R^{12}$, $R^{12'}$, $R^{13}$, $R^{13'}$, $R^{14}$, $R^{14'}$, $R^{15}$, $R^{15'}$, $R^{16}$, and $R^{16'}$ is independently hydrogen or $C_1$-$C_{10}$ hydrocarbyl. In at least one embodiment, each of $R^1$, $R^{1'}$, $R^2$, $R^{2'}$, $R^3$, $R^{3'}$, $R^4$, $R^{4'}$, $R^5$, $R^{5'}$, $R^6$, $R^{6'}$, $R^7$, $R^8$, $R^{11}$, $R^{11'}$, $R^{12}$, $R^{12'}$, $R^{13}$, $R^{13'}$, $R^{14}$, $R^{14'}$, $R^{15}$, $R^{15'}$, $R^{16}$, and $R^{16'}$ is hydrogen. $R^7$ and $R^8$ can be hydrogen. $R^9$ and $R^{10}$ are independently hydrogen or an end cap. End caps include ether, amine, aryl, or carboxylic acid. Ether includes ethyl ether, propyl ether, butyl ether, pentyl ether, or hexyl ether.

In at least one embodiment, a polymer is a poly-[cyclopentene]-[cyclooctene] is represented by Formula (V):

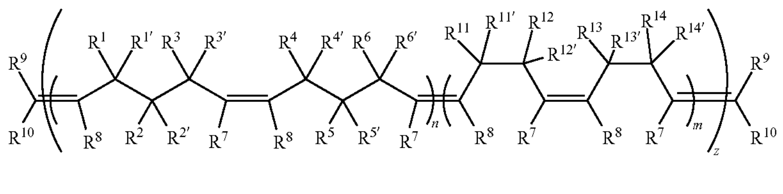

(V)

each of n, m, and z is a positive integer. In one embodiment, n is from about 1 to about 25,000, such as from about 500 to about 5,000, such as from about 2,500 to about 4,000. m is from about 1 to about 25,000, such as from about 500 to about 5,000, such as from about 2,500 to about 4,000. z is from about 1 to about 5,000, such as from about 100 to about 3,000, such as from about 300 to about 1,000. Each of $R^1$, $R^{1'}$, $R^2$, $R^{2'}$, $R^3$, $R^{3'}$, $R^4$, $R^{4'}$, $R^5$, $R^{5'}$, $R^6$, $R^{6'}$, $R^7$, $R^8$, $R^{11}$, $R^{11'}$, $R^{12}$, $R^{12'}$, $R^{13}$, $R^{13'}$, $R^{14}$, and $R^{14'}$ is independently hydrogen, $C_1$-$C_{40}$ hydrocarbyl, or $R^1$ and $R^2$, $R^1$ and $R^3$, $R^2$ and $R^3$, $R^4$ and $R^5$, $R^5$ and $R^6$, $R^{11}$ and $R^{12}$, or $R^{13}$ and $R^{14}$ join together to form a saturated or unsaturated cyclic $C_5$-$C_{10}$ hydrocarbyl. In at least one embodiment, each of $R^1$, $R^{1'}$, $R^2$, $R^{2'}$, $R^3$, $R^{3'}$, $R^4$, $R^{4'}$, $R^5$, $R^{5'}$, $R^6$, $R^{6'}$, $R^7$, $R^8$, $R^{11}$, $R^{11'}$, $R^{12}$, $R^{12'}$, $R^{13}$, $R^{13'}$, $R^{14}$, and $R^{14'}$ is independently hydrogen or $C_1$-$C_{10}$ hydrocarbyl. In at least one embodiment, each of $R^1$, $R^{1'}$, $R^2$, $R^{2'}$, $R^3$, $R^{3'}$, $R^4$, $R^{4'}$, $R^5$, $R^{5'}$, $R^6$, $R^{6'}$, $R^7$, $R^8$, $R^{11}$, $R^{11'}$, $R^{12}$, $R^{12'}$, $R^{13}$, $R^{13'}$, $R^{14}$, and $R^{14'}$ is hydrogen. $R^7$ and $R^8$ can be hydrogen. $R^9$ and $R^{10}$ are independently hydrogen or an end cap. End caps include ether, amine, aryl, or carboxylic acid. Ether includes ethyl ether, propyl ether, butyl ether, pentyl ether, or hexyl ether.

The polymers represented by Formulas (I)-(V) above may have any suitable amount of cis carbon-carbon double bonds and trans carbon-carbon double bonds. In general, the trans conformation is thermodynamically favored, such that the trans carbon-carbon double bonds of a polymer typically constitute greater than 50% of total double bonds of the polymer. Nonetheless, it has been discovered that, in light of the high yields of cyclic olefins of processes of the present disclosure, the cis vs. trans content of an unsaturated polymer starting material merely can affect the reaction rate of the process and has little or no effect on the overall yield of cyclic olefin products.

Polymer starting materials can be those that are vulcanized (e.g., cross-linked) or not vulcanized. Polymer starting materials can be obtained from any suitable source, such as can be synthesized or obtained from a polymer source. For example, a polymer may be obtained from various parts of a tire, for example, tires, tire treads, tire sidewalls, wire-skim for tires, and cushion gum for retread tires. Alternatively or in addition, a polymer may be obtained from hoses, seals, gaskets, anti-vibration articles, tracks, track pads for track-propelled equipment such as bulldozers, etc., engine mounts, earthquake stabilizers, mining equipment such as screens, mining equipment linings, conveyor belts, chute liners, slurry pump liners, mud pump components such as impellers, valve seats, valve bodies, piston hubs, piston rods, plungers, impellers for various applications such as mixing slurries and slurry pump impellers, grinding mill liners, cyclones and hydro-cyclones, expansion joints, marine equipment such as linings for pumps (e.g., dredge pumps and outboard motor pumps), hoses (e.g., dredging hoses and outboard motor hoses), and other marine equipment, shaft seals for marine, oil, aerospace, and other sources, propeller shafts, linings for piping to convey, e.g., oil sands and/or tar sands, and other applications. The a polymer may be obtained from any suitable part of rollers, cams, shafts, pipes, tread bushings for vehicles, or other sources.

Other sources of polymer starting materials may include molded products. Molded products are those that have been produced using any suitable molding process, including but not limited to, injection molding, gas-assisted injection molding, extrusion blow molding, injection blow molding, injection stretch blow molding, compression molding, rotational molding, foam molding, thermoforming, sheet extrusion, and profile extrusion. The polymers can be those that have been shaped into desirable end use articles by any suitable means. Suitable examples include thermoforming, vacuum forming, blow molding, rotational molding, slush molding, transfer molding, wet lay-up or contact molding, cast molding, cold forming matched-die molding, injection molding, spray techniques, profile co-extrusion, or combinations thereof.

The polymer may be obtained from suitable nonwoven fabrics or fibers, such as those that have been formed using melt blowing, spunbonding, film aperturing, and staple fiber carding. Other sources of polymer starting material include automotive overshoot parts (e.g., door handles and skins such as dashboard, instrument panel and interior door skins), house tool handles, airbag covers, toothbrush handles, shoe soles, grips, skins, toys, appliance moldings and fascia, gaskets, furniture moldings and the like. Other sources include awnings and canopies—coated fabric, tents/tarps coated fabric covers, curtains extruded soft sheet, protective cloth coated fabric, bumper fascia, instrument panel and trim skin, coated fabric for auto interior, geo textiles, appliance door gaskets, liners/gaskets/mats, hose and tubing, syringe plunger tips, light weight conveyor belt PVC replacement, modifier for rubber concentrates to reduce viscosity, single ply roofing compositions, recreation and sporting goods, grips for pens, razors, toothbrushes, handles, and the like. Other sources of polymer include marine belting, pillow tanks, ducting, dunnage bags, architectural trim and molding, collapsible storage containers, synthetic wine corks, IV and fluid administration bags, examination gloves, and the like. Other sources of polymer include cookware, storage ware, toys, medical devices, sterilizable medical devices, sterilization containers, sheets, crates, containers, packaging, wire and cable jacketing, pipes, geomembranes, sporting equipment, chair mats, tubing, profiles, instrumentation sample holders and sample windows, outdoor furniture, e.g., garden furniture, playground equipment, automotive, boat and water craft components, and other such articles. In particular, sources of polymer can include automotive components such as bumpers, grills, trim parts, dashboards and instrument panels, exterior door and hood components, spoiler, wind screen, hub caps, mirror housing, body panel, protective side molding, and other interior and external components associated with automobiles, trucks, boats, and other vehicles. Other polymer sources include personal care articles such as toothbrushes, etc.; toys; small appliances; packaging; kitchenware; sport and leisure products; consumer electronics; medical tubing; industrial hoses; and shower tubing.

Vulcanization

As mentioned above, polymer starting materials of the present disclosure can be vulcanized polymers. Vulcanized polymers are typically formed using any of a variety of curatives to form crosslinked polymers. Exemplary curatives can include ultraviolet cure, sulfur cure systems, phenolic resin cure systems, peroxide cure systems, silicon-containing cure systems, such as hydrosilylation and silane grafting/moisture cure.

Vulcanization can be effected by mixing the polymer, an optional other polymer (e.g., polypropylene), and curative(s) at elevated temperature in conventional mixing equipment such as roll mills, stabilizers, Banbury mixers, Brabender mixers, continuous mixers, mixing extruders and the like.

In some embodiments, useful peroxide curatives can include organic peroxides. Examples of organic peroxides can include di-tert-butyl peroxide, dicumyl peroxide, t-butylcumyl peroxide, α,α-bis(tert-butylperoxy) diisopropyl benzene, 2,5-dimethyl-2,5-di(t-butylperoxy)hexane (DBPH), 1,1-di(tert-butylperoxy)-3,3,5-trimethyl cyclohexane, n-butyl-4-4-bis(tert-butylperoxy) valerate, benzoyl peroxide, lauroyl peroxide, dilauroyl peroxide, 2,5-dimethyl-2,5-di(tert-butylperoxy) hexyne-3, and mixtures thereof. Also, diaryl peroxides, ketone peroxides, peroxydicarbonates, peroxyesters, dialkyl peroxides, hydroperoxides, peroxyketals and mixtures thereof may be used. Useful peroxides and their processes of use in vulcanization are disclosed in U.S. Pat. No. 5,656,693, which is incorporated herein by reference.

In some embodiments, the peroxide curatives can be employed in conjunction with a coagent. Examples of coagents can include triallylcyanurate, triallyl isocyanurate, triallyl phosphate, sulfur, N-phenyl bis-maleamide, zinc diacrylate, zinc dimethacrylate, divinyl benzene, 1,2-polybutadiene, trimethylol propane trimethacrylate, tetramethylene glycol diacrylate, trifunctional acrylic ester, dipentaerythritolpentacrylate, polyfunctional acrylate, retarded cyclohexane dimethanol diacrylate ester, polyfunctional methacrylates, acrylate and methacrylate metal salts, and oximes such as quinone dioxime. The mixing and dynamic vulcanization may be carried out in a nitrogen atmosphere.

Alternatively, a sulfur source may be used to effect crosslinking. Examples of sulfur sources include elemental sulfur.

Alternatively, crosslinking may be accomplished by exposing a polymer to electromagnetic radiation having a frequency greater than that of visible light, such as for example near ultraviolet radiation, extreme ultraviolet radiation, soft x-rays, hard x-rays, gamma rays, and high-energy gamma rays. In some embodiments, crosslinking is accomplished by electron beam radiation, or "e-beam" radiation.

E-beam radiation is a form of ionizing energy that is generally characterized by its low penetration and high dose rates. The electrons can be generated by equipment referred to as accelerators which are capable of producing beams that are either pulsed or continuous. The term "beam" is meant to include any area exposed to electrons, which may range from a focused point to a broader area, such as a line or field. A photo-initiator may be added to (e.g., mixed with) the copolymer (or ICP) to promote crosslinking upon exposure to electromagnetic radiation. Suitable photo-initiators include ketones (such as 1-hydroxycyclohexyl phenyl ketone), 2,2-diethoxyacetophenone, 4'-hydroxy-3',5'-dimethylacetophenone, 2,2-dimethoxy-2-phenylacetophenone, or 1-benzoylcyclohexanol.

A method for determining the degree of crosslinking is disclosed in U.S. Pat. No. 4,311,628, which is incorporated herein by reference. In some embodiments, a polymer is fully crosslinked or partially crosslinked. For example, a polymer can be partially crosslinked such that the polymer has a degree of crosslinking where not more than about 5.9 wt %, such as not more than about 5 wt %, such as not more than about 4 wt %, such as not more than about 3 wt % is extractable by cyclohexane at 23° C. as described in U.S. Pat. Nos. 5,100,947 and 5,157,081, which are incorporated herein by reference. In these or other embodiments, the polymer is crosslinked to an extent where greater than about 94 wt %, such as greater than about 95 wt %, such as greater than about 96 wt %, such as greater than about 97 wt % by weight of the copolymer is insoluble in cyclohexane at 23° C.

Polymer starting materials of the present disclosure can be partially vulcanized. A "partially vulcanized" polymer is one where more than 5 weight percent (wt %) of the cross-linkable copolymer is extractable in boiling xylene, subsequent to vulcanization. For example, a partially vulcanized polymer starting material can have at least 5 wt % and less than 20 wt %, or 30 wt %, or 50 wt % of the cross-linkable polymer that is extractable from the polymer sample in boiling xylene.

Additives

Polymer starting materials (e.g., vulcanized rubber) of the present disclosure may include one or more additives. The additives may include reinforcing and non-reinforcing fillers, antioxidants, stabilizers, processing oils (or other diluent (s)), compatibilizing agents, lubricants (e.g., oleamide), antiblocking agents, antistatic agents, waxes, coupling agents for the fillers and/or pigment, pigments, flame retardants, antioxidants, or other processing aids, or combination(s) thereof.

In some embodiments, the polymer starting material may include fillers and coloring agents. Exemplary materials include inorganic fillers such as calcium carbonate, clays, silica, talc, titanium dioxide or carbon black. Any type of carbon black can be present, such as channel blacks, furnace blacks, thermal blacks, acetylene black, lamp black and the like.

In some embodiments, the polymer starting material may include flame retardants, such as calcium carbonate, inorganic clays containing water of hydration such as aluminum trihydroxides ("ATH") or magnesium hydroxide.

In some embodiments, the polymer starting material may include UV stabilizers, such as titanium dioxide or Tinuvin® XT-850. Still other additives may include antioxidant and/or thermal stabilizers. In an exemplary embodiment, processing and/or field thermal stabilizers may include IRGANOX® B-225 and/or IRGANOX® 1010 available from BASF.

In some embodiments, the polymer starting material may include a polymeric processing additive. These polymeric resins can include both linear and branched polymers that can have a melt flow rate that is about 500 dg/min or more, such as about 750 dg/min or more, such as about 1000 dg/min or more, such as about 1200 dg/min or more, such as about 1500 dg/min or more. Mixtures of various branched or various linear polymeric processing additives, as well as mixtures of both linear and branched polymeric processing additives, can be employed. Linear polymeric processing additives can include polypropylene homopolymers, and branched polymeric processing additives can include diene-modified polypropylene polymers.

Fillers and extenders that can be present in the polymer starting material include conventional inorganics such as calcium carbonate, clays, silica, talc, titanium dioxide, carbon black, a nucleating agent, mica, wood flour, and the like, and blends thereof, as well as inorganic and organic nanoscopic fillers.

Polymer Blends

In some embodiments, the polymer starting material can further include one or more additional polymers. The additional polymer(s) may be included in a vulcanized form with the first polymer. Alternatively, a mixture of the first polymer and additional polymer may be unvulcanized. For depolymerization, the additional polymer(s) may be depolymerized to form cyclic olefin(s), may be unreactive in the presence of catalysts of the present disclosure, or may react to form other product(s). Preferably, the additional polymer (s) react to form cyclic olefin(s) or are unreactive in the presence of catalysts of the present disclosure. Additional polymer(s) can include polyethylene, isotactic polypropylene, highly isotactic polypropylene, syndiotactic polypropylene, random copolymer of propylene and ethylene, and/or butene, and/or hexene, polybutene, ethylene vinyl acetate, LDPE, LLDPE, HDPE, ethylene vinyl acetate, ethylene methyl acrylate, copolymers of acrylic acid, polymethylmethacrylate or any other polymers polymerizable by a high-pressure free radical process, polyvinylchloride, polybutene-1, isotactic polybutene, ABS resins, ethylene-propylene rubber (EPR), vulcanized EPR, EPDM, block copolymer, styrenic block copolymers, polyamides, polycarbonates, PET resins, cross linked polyethylene, copolymers of ethylene and vinyl alcohol (EVOH), polymers of aromatic monomers such as polystyrene, poly-1 esters, polyacetal, polyvinylidine fluoride, polyethylene glycols, and/or polyisobutylene.

In some embodiments, the additional polymer is present in the above blends, at from 0.1 to 99 wt %, based upon the weight of the polymers in the blend, such as 0.1 to 60 wt %, such as 0.1 to 50 wt %, such as 1 wt % to 40 wt %, such as 1 to 30 wt %, such as 1 to 20 wt %, such as 1 to 10 wt %.

The blends described above may be produced by mixing the polymers with one or more additional polymers (as described above), by connecting reactors together in series to make reactor blends or by using more than one catalyst in the same reactor to produce multiple species of polymer. The polymers can be mixed together prior to being put into an extruder or may be mixed in an extruder.

The blends may be formed using conventional equipment and processes, such as by dry blending the individual components and subsequently melt mixing in a mixer, or by mixing the components together directly in a mixer, such as, for example, a Banbury mixer, a Haake mixer, a Brabender internal mixer, or a single or twin-screw extruder, which may include a compounding extruder and a side-arm extruder used directly downstream of a polymerization process, which may include blending powders or pellets of the resins at the hopper of the film extruder. Additionally, additives (e.g., as described above) may be included in the blend, in one or more components of the blend, and/or in a product formed from the blend, such as a film, as desired. Such additives may include, for example: fillers; antioxidants (e.g., hindered phenolics such as IRGANOX™ 1010 or IRGANOX™ 1076 available from Ciba-Geigy); phosphites (e.g., IRGAFOS™ 168 available from Ciba-Geigy); anti-cling additives; tackifiers, such as polybutenes, terpene resins, aliphatic and aromatic hydrocarbon resins, alkali metal and glycerol stearates, and hydrogenated rosins; UV stabilizers; heat stabilizers; anti-blocking agents; release agents; anti-static agents; pigments; colorants; dyes; waxes; silica; fillers; talc; and the like.

Polymer Isomerization and Depolymerization Processes

Cyclic olefins of the present disclosure may be produced using processes where polymer starting material is contacted with a catalyst compound (optionally having a support material where the catalyst is a supported catalyst). The catalyst compound with optional support material may be combined in any order, and are combined typically prior to contacting with the polymer starting material. A catalyst compound can promote polymer isomerization and/or depolymerization to provide cyclic olefin products.

In embodiments, where a polymer starting material is a polymer obtained from an article of manufacture (e.g., a polymer starting material intended for recycle where the polymer starting material is obtained from an article as described above), the polymer article can be optionally ground into smaller particles, e.g. using any suitable method such as pulverizing, mortar and pestel, a blunger, cutting, cryogrinded etc. The smaller size of the particles formed promotes faster depolymerization. Advantageously, the particles may need little or no pretreatment (e.g., removal of metal, devulcanization at elevated temperature, etc.) before isomerization and/or depolymerization due to the propensity of catalysts of the present disclosure to resist catalyst poisoning from additives present in the polymer starting material.

Some embodiments herein relate to processes wherein the depolymerization is a ring closing metathesis reaction including: (i) contacting an optionally cured unsaturated polymer starting material with a metathesis catalyst under conditions and for a time period sufficient to allow the ring closing metathesis reaction to occur; and (ii) obtaining a ring closing metathesis product (such as the ring closing metathesis product is a monomer unit of the unsaturated polymer and is obtained in greater than 50 mol % yield, such as in greater than 60 mol % yield, such as in greater than 70 mol % yield, such as in greater than 75 mol % yield, such as in greater than 80 mol % yield, such as in greater than 90 mol % yield, such as in greater than 95 mol %, such as in greater than 99 mol % yield, such as in greater than 99.9 mol % yield), based on the amount of polymer starting material.

In at least one embodiment, the reactants (for example, metathesis catalyst; unsaturated polymer, optional diluent, etc.) are combined in a reaction vessel at a temperature of 20° C. to 300° C. (such as 20° C. to 200° C., such as 30° C. to 100° C., such as 40° C. to 60° C., alternatively 55° C. to 85° C.) and/or at a pressure of 0.1 psig to 1,000 psi (0.7 kPa to 6.9 MPa) (such as 20 to 400 psi (0.14 MPa to 2.8 MPa), such as 50 to 250 psi (0.34 MPa to 1.7 MPa)), and/or for a residence time of 0.5 seconds to 48 hours (such as 0.25 seconds to 5 hours, such as 30 minutes to 2 hours).

In at least one embodiment of ring closing metathesis, the catalyst is present at from 0.001 nanomoles of transition metal per mole of unsaturated polymer to 1 millimole of transition metal per mole of unsaturated polymer, based upon the moles of unsaturated polymer feed into the reactor. Alternately, the catalyst is present at from 0.01 nanomoles of transition metal per mole of unsaturated polymer to 0.1 millimole of transition metal per mole of unsaturated polymer, alternately from 0.1 nanomoles of transition metal unsaturated polymer to 0.075 millimole of transition metal per mole of unsaturated polymer, based upon the moles of unsaturated polymer feed into the reactor.

Processes of the present disclosure can be batch, semi-batch or continuous. As used herein, the term continuous means a system that operates without interruption or cessation. For example, a continuous process to produce cyclic olefins would be one where the reactants are continually introduced into one or more reactors and polymer product is continually withdrawn.

The processes for depolymerization (and optional isomerization) may be conducted in any suitable reaction vessel, such as glass lined, stainless steel, or similar type reaction equipment. Useful reaction vessels include reactors (including continuous stirred tank reactors, batch reactors, reactive extruder, pipe, or pump, continuous flow fixed bed reactors, slurry reactors, fluidized bed reactors, and catalytic distillation reactors). The reaction zone may be fitted with one or more internal and/or external heat exchanger(s) in order to control undue temperature fluctuations, or to prevent "run-away" reaction temperatures.

The quantity of catalyst that is employed in a depolymerization (or isomerization) is any quantity that provides for an operable metathesis reaction. The ratio of moles of monomer units of a polymer (of the polymer starting material) to moles of catalyst can be typically greater than about 10:1, such as greater than about 100:1, such as greater than about 1000:1, such as greater than about 10,000:1, such as greater than about 25,000:1, such as greater than about 50,000:1, such as greater than about 100,000:1. Alternately, the molar ratio of monomer units of a polymer to catalyst is less than about 10,000,000:1, such as less than about 1,000,000:1, such as less than about 500,000:1.

The contacting time of the reagents and catalyst in a batch reactor can be any duration, provided that the cyclic olefin products are obtained. Generally, the contacting time in a reactor is greater than about 5 minutes, such as greater than about 10 minutes. Generally, the contacting time in a reactor is less than about 25 hours, such as less than about 15 hours, such as less than about 10 hours. Alternatively, the optional isomerization and/or depolymerization are performed as a continuous process that extends beyond 25 hours.

In at least one embodiment, the reactants (for example, metathesis catalyst; polymer starting material) are combined in a reaction vessel at a temperature of 20° C. to 300° C. (such as 20 to 200° C., such as 30 to 100° C., such as 55 to 85° C.) and a pressure of 0.1 to 1,000 psi (0.7 kPa to 6.9 MPa) (such as 20 to 400 psi (0.14 MPa to 2.8 MPa), such as 50 to 250 psi (0.34 MPa to 1.7 MPa)), for a residence time of 0.5 seconds to 48 hours (such as 0.25 to 5 hours, such as 2 hours to 4 hours).

Typically, the conversion of the polymer starting material is greater than about 50 mole percent, such as greater than about 60 mole percent, such as greater than about 70 mole percent, such as greater than about 80 mole percent, such as greater than about 90 mole percent, such as greater than about 95 mole percent, based on the moles of polymer capable of being depolymerized.

In at least one embodiment, the process is a solution process, although it may be a bulk or high pressure process. (A homogeneous process is defined to be a process where at least 90 wt % of the product is soluble in the reaction media.) A bulk homogeneous process can also be used. (A bulk process is defined to be a process where reactant concentration in all feeds to the reactor is 70 volume % or more.) Alternately, no diluent is present or added in the reaction medium, (except for the optional small amounts used as the carrier for the catalyst or other additives, or amounts typically found with the reactants).

In at least one embodiment, an isomerization or depolymerization is performed as a slurry process. For example, an oil or wax is used as a stirring diluent and lubricant, and the polymer starting material and/or catalyst(s) are heterogeneous in the diluent.

In at least one embodiment, the feed concentration of the polymer starting material for the depolymerization is 60 vol % diluent or less, such as 40 vol % or less, or such as 20 vol % or less, based on the total volume of the feedstream. In at least one embodiment, the depolymerization is run in a bulk process.

Suitable diluents for isomerization and/or depolymerization include non-coordinating, inert liquids. Examples include straight and branched-chain hydrocarbons, such as isobutane, butane, pentane, isopentane, hexanes, isohexane, heptane, octane, dodecane, and mixtures thereof; cyclic and alicyclic hydrocarbons, such as cyclohexane, cycloheptane, methylcyclohexane, methylcycloheptane, and mixtures thereof, such as can be found commercially (Isopar™, SpectraSyn2 or SpectraSyn4); perhalogenated hydrocarbons, such as perfluorinated $C_{4-10}$ alkanes, chlorobenzene, and aromatic and alkylsubstituted aromatic compounds, such as benzene, toluene, mesitylene, and xylene. Suitable diluents also include liquid olefins which may act as monomers or comonomers including ethylene, propylene, 1-butene, 1-hexene, 1-pentene, 3-methyl-1-pentene, 4-methyl-1-pentene, 1-octene, 1-decene, and mixtures thereof. In at least one embodiment, aliphatic hydrocarbon diluents are used as the diluent, such as isobutane, butane, pentane, isopentane, hexanes, isohexane, heptane, octane, dodecane, and mixtures thereof; cyclic and alicyclic hydrocarbons, such as cyclohexane, cycloheptane, methylcyclohexane, methylcycloheptane, and mixtures thereof. In another embodiment, the diluent is not aromatic, such as aromatics are present in the diluent at less than 1 wt %, such as less than 0.5 wt %, such as less than 0 wt % based upon the weight of the diluent.

In some embodiments, an oil or wax is used as a diluent. Advantageously, oil or wax diluents typically have a higher boiling point than lower molecular weight diluents (such as hexanes) which allows cyclic olefin products formed during a depolymerization to be readily isolated from the reaction mixture. Oil and wax diluents are particularly advantageous for continuous processes where cyclic olefin products are continuously removed from the reactor.

A wax can be a paraffin wax. Paraffin waxes include SONO JELL® paraffin waxes, such as SONO JELL® 4 and SONO JELL® 9 from Sonneborn, LLC. In at least one embodiment, a slurry has 5 wt % or greater of wax, such as 10 wt % or greater, such as 25 wt % or greater, such as 40 wt % or greater, such as 50 wt % or greater, such as 60 wt % or greater, such as 70 wt % or greater. In at least one embodiment, a wax has a density of from about 0.7 $g/cm^3$ (at 100° C.) to about 0.95 $g/cm^3$ (at 100° C.), such as from about 0.75 $g/cm^3$ (at 100° C.) to about 0.87 $g/cm^3$ (at 100° C.). A wax can have a kinematic viscosity of from 5 $mm^2/s$ (at 100° C.) to about 30 $mm^2/s$ (at 100° C.). A wax can have a boiling point of about 200° C. or greater, such as about 225° C. or greater, such as about 250° C. or greater. A wax can have a melting point of from about 25° C. to about 100° C., such as from about 35° C. to about 80° C.

Paraffin waxes can include SONO JELL® paraffin waxes, such as SONO JELL® 4 and SONO JELL® 9 from Sonneborn, LLC. SONO JELL® paraffin waxes are compositions that typically contain 10 wt % or more of wax and up to 90 wt % of mineral oil. For example, a SONO JELL® paraffin wax can be 20 wt % wax and 80 wt % mineral oil. In at least one embodiment, a slurry has 5 wt % or greater of wax, such as 10 wt % or greater, such as 25 wt % or greater, such as 40 wt % or greater, such as 50 wt % or greater, such as 60 wt % or greater, such as 70 wt % or greater.

Mineral oil can have a density of from 0.85 g/cm$^3$ to 0.9 g/cm$^3$ at 25° C. according to ASTM D4052, such as from 0.86 g/cm$^3$ to 0.88 g/cm$^3$. Mineral oil can have a kinematic viscosity at 25° C. of from 150 cSt to 200 cSt according to ASTM D341, such as from 160 cSt to 190 cSt, such as about 170 cSt. Mineral oil can have an average molecular weight of from 400 g/mol to 600 g/mol according to ASTM D2502, such as from 450 g/mol to 550 g/mol, such as about 500 g/mol. In at least one embodiment, a mineral oil is HYDROBRITE® 380 PO White Mineral Oil ("HB380") from Sonneborn, LLC.

In at least one embodiment, the activity of a depolymerization catalyst is at least 800 g-cyclic olefin/g-catalyst/hour, such as 1,000 or more g-cyclic olefin/g-catalyst/hour, such as 1,200 or more g-cyclic olefin/g-catalyst/hour, such as 1,600 or more g-cyclic olefin/g-catalyst/hour.

Unlike ring opening metathesis polymerizations, ring closing metathesis depolymerizations of the present disclosure can be free of added quench agent. Quench agents are typically used in ring opening metathesis polymerizations to terminate a polymerization and provide end caps to a polymer product. Quench agents typically used in ring opening metathesis polymerizations are typically ethers, vinylene carbonate, 3H-furanones, amines, or benzaldehydes. Similarly, unlike olefin polymerizations to form polyolefins, depolymerizations of the present disclosure can be free of added hydrogen, scavengers, promoters, modifiers, chain transfer agents, reducing agents, oxidizing agents, aluminum alkyls, or silanes. For example, hydrogen is typically used in olefin polymerizations to control molecular weight of the polyolefins that are produced.

Slurry Phase Depolymerization

A slurry depolymerization can be performed as a suspension of solid, particulate polymer is introduced in a liquid diluent to which catalyst is added. The suspension including diluent is intermittently or continuously removed from the reactor where the volatile components are separated from the polymer and catalyst. As mentioned above, the diluent may be a wax or oil or any other suitable diluent (such as hexane). The diluent employed should be liquid under the conditions of depolymerization and relatively inert.

In an embodiment, a depolymerization technique herein is referred to as a particle form depolymerization, or a slurry process where the temperature is kept below the temperature at which the polymer goes into solution. Non-limiting examples of slurry processes include stirred tank processes.

In another embodiment, the slurry process is carried out continuously in a loop or tubular reactor. The catalyst, as a slurry in diluent or as a dry free flowing powder, is injected regularly to the reactor loop, which is itself filled with circulating slurry of depolymerizing polymer particles in a diluent.

The slurry is allowed to exit the reactor at regular intervals or continuously to a heated low pressure flash vessel, rotary dryer and a nitrogen purge column in sequence for removal of low boiling diluents and/or cyclic olefin products from any remaining polymer starting material and/or catalysts.

Solution Depolymerization

In at least one embodiment, the depolymerization process (and/or optional isomerization process) is a solution depolymerization process.

A solution depolymerization is a depolymerization process in which the polymer is dissolved in a liquid depolymerization medium, such as an inert diluent. A solution depolymerization is typically homogeneous. A homogeneous depolymerization is one where the polymer starting material is dissolved in the depolymerization medium. Solution depolymerization may involve depolymerization in a continuous reactor in which the polymer, the cyclic olefin products, and catalyst materials supplied are agitated to reduce or avoid concentration gradients and in which the cyclic olefin product acts as a diluent. The diluent can be also introduced as a catalyst carrier. The diluent can be introduced as a gas phase or as a liquid phase depending on the pressure and temperature. Advantageously, the diluent can be kept in the liquid phase and introduced as a liquid. Diluent can be introduced in the feed to the polymerization reactors.

A process described herein can be a solution depolymerization process that may be performed in a batchwise fashion (e.g., batch; semi-batch) or in a continuous process. Suitable reactors may include tank, loop, and tube designs. In at least one embodiment, the process is performed in a continuous fashion and dual loop reactors in a series configuration are used. In at least one embodiment, the process is performed in a continuous fashion and dual continuous stirred-tank reactors (CSTRs) in a series configuration are used. Furthermore, the process can be performed in a continuous fashion and a tube reactor can be used. In another embodiment, the process is performed in a continuous fashion and one loop reactor and one CSTR are used in a series configuration. The process can also be performed in a batchwise fashion and a single stirred tank reactor can be used.

Depolymerization Catalysts

A catalyst's resistance to catalyst poisoning can be an important consideration for industrial scale up of recycling rubber because commercial rubbers typically contain many different types (sometimes in large amounts) of additives. It has been discovered that catalysts used for depolymerization processes of the present disclosure can have a low propensity for catalyst poisoning when in the presence of commercial rubber, for example without pretreating the rubber. It has also been discovered that depolymerization catalysts of the present disclosure can provide cyclic olefins in high yield even with vulcanized (e.g., partially, highly, or completely crosslinked) rubbers.

Catalysts of the present disclosure can have a long catalyst lifetime, which provides process and economic advantages for industrial scale up of processes of the present disclosure. Nonetheless, catalysts of the present disclosure may also be refurbished (e.g., upon eventual deactivation (if any)) by reclaiming the metal of the catalyst from the catalyst ligand(s). The catalyst metal can be isolated and new depolymerization catalyst can be formed.

Furthermore, it has been discovered that, in some embodiments, catalysts of the present disclosure may also provide a dual functionality of (1) polymer isomerization in addition to (2) ring closing metathesis for formation of cyclic olefins. The dual functionality is advantageous in that a catalyst that eventually deactivates, for example for ring closing metathesis, may nonetheless still be active for polymer isomerization. Alternatively, an isomerization catalyst can be used in addition to the ring closing metathesis catalyst. Scheme 1 below illustrates a non-limiting example of isomerization and depolymerization of polyalkenamer to provide a mixed product of 1,2-dimethylcyclopentene and 3-methylcyclopentene.

Scheme 1

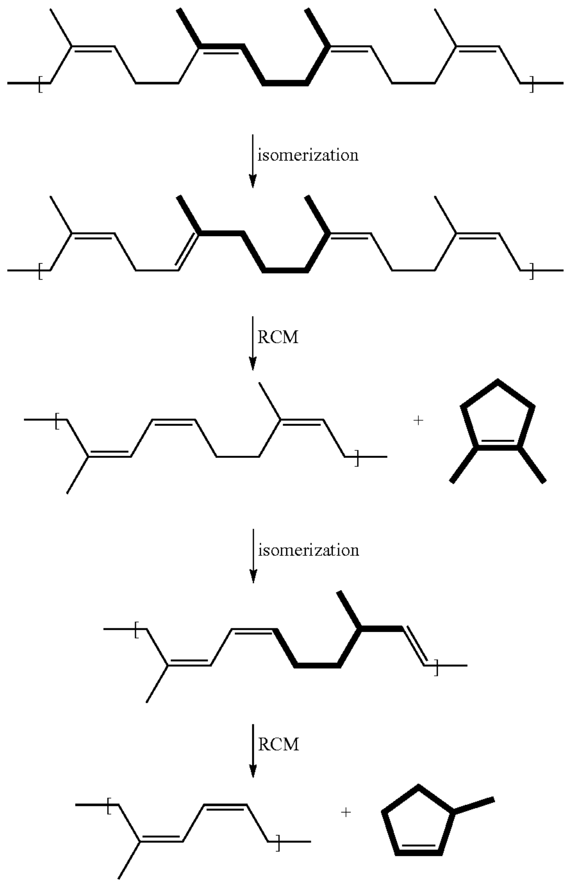

In some embodiments, depolymerization catalysts of the present disclosure may be capable of performing isomerization processes as well as depolymerization.

Depolymerization catalysts of the present disclosure for forming cyclic olefins can be metathesis catalysts. In some embodiments, the metathesis catalyst is represented by the Formula (VI):

(VI)

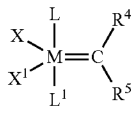

where

M is a Group 8 metal, such as Ru or Os, such as Ru;

X and $X^1$ are, independently, any anionic ligand, such as a halogen (such as chlorine), an alkoxide or a triflate, or X and $X^1$ may be joined to form a dianionic group and may form a single ring of up to 30 non-hydrogen atoms or a multinuclear ring system of up to 30 non-hydrogen atoms;

L and $L^1$ are, independently, a neutral two electron donor, such as a phosphine or a N-heterocyclic carbene, L and $L^1$ may be joined to form a single ring of up to 30 non-hydrogen atoms or a multinuclear ring system of up to 30 non-hydrogen atoms;

L and X may be joined to form a multidentate monoanionic group and may form a single ring of up to 30 non-hydrogen atoms or a multinuclear ring system of up to 30 non-hydrogen atoms;

$L^1$ and $X^1$ may be joined to form a multidentate monoanionic group and may form a single ring of up to 30 non-hydrogen atoms or a multinuclear ring system of up to 30 non-hydrogen atoms;

$R^4$ and $R^5$ are, independently, hydrogen or $C_1$ to $C_{30}$ substituted or unsubstituted hydrocarbyl (such as a $C_1$ to $C_{30}$ substituted or unsubstituted alkyl or a substituted or unsubstituted $C_4$ to $C_{30}$ aryl);

$R^5$ and $L^1$ or $X^1$ may be joined to form a single ring of up to 30 non-hydrogen atoms or a multinuclear ring system of up to 30 non-hydrogen atoms; and $R^4$ and L or X may be joined to form a single ring of up to 30 non-hydrogen atoms or a multinuclear ring system of up to 30 non-hydrogen atoms.

Example alkoxides include those where the alkyl group is a phenol, substituted phenol (where the phenol may be substituted with up to 1, 2, 3, 4, or 5 $C_1$ to $C_{12}$ hydrocarbyl groups) or a $C_1$ to $C_{10}$ hydrocarbyl, such as a $C_1$ to $C_{10}$ alkyl group, such as methyl, ethyl, propyl, butyl, or phenyl.

Example phosphines are represented by the formula: $PR^{3'}R^{4'}R^{5'}$, where $R^{3'}$ is a secondary alkyl or cycloalkyl (such as a $C_3$ to $C_{12}$ secondary alkyl or cycloalkyl), and $R^{4'}$ and $R^{5'}$ are aryl, $C_1$ to $C_{10}$ primary alkyl, secondary alkyl, or cycloalkyl. $R^{4'}$ and $R^{5'}$ may be the same or different. Example phosphines can include $P(cyclohexyl)_3$, $P(cyclopentyl)_3$, and/or $P(isopropyl)_3$.

Example triflates are represented by the Formula (VII):

Formula (VII)

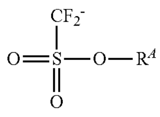

where $R^A$ is hydrogen or a $C_1$ to $C_{30}$ hydrocarbyl group, such as a $C_1$ to $C_{12}$ alkyl group, such as methyl, ethyl, propyl, butyl, or phenyl.

Example N-heterocyclic carbenes are represented by the Formula (VIII) or the Formula (IX):

Formula (VIII)

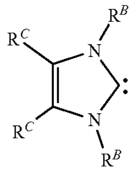

or

-continued

Formula (IX)

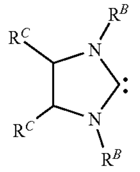

where each $R^B$ is independently a hydrocarbyl group or substituted hydrocarbyl group having 1 to 40 carbon atoms, such as methyl, ethyl, propyl, butyl (including iso-butyl and n-butyl), pentyl, cyclopentyl, hexyl, cyclohexyl, octyl, cyclooctyl, nonyl, decyl, cyclodecyl, dodecyl, cyclododecyl, mesityl, adamantyl, phenyl, benzyl, tolulyl, chlorophenyl, phenol, substituted phenol, or $CH_2C(CH_3)_3$; and each $R^C$ is hydrogen, a halogen, or a $C_1$ to $C_{12}$ hydrocarbyl group, such as hydrogen, bromine, chlorine, methyl, ethyl, propyl, butyl, or phenyl.

In other useful embodiments, one of the N groups bound to the carbene in Formula (VIII) or (IX) is replaced with an S, O, or P atom, such as an S atom.

Other useful N-heterocyclic carbenes and their heavier analogues include the compounds described in Hermann, W. A. *Chem. Eur. J.,* 1996, 2, pp. 772 and 1627; Enders, D. et al. *Angew. Chem. Int. Ed.,* 1995, 34, pg. 1021; Alder R. W., *Angew. Chem. Int. Ed.,* 1996, 35, pg. 1121; Bertrand, G. et al., *Chem. Rev.,* 2000, 100, pg. 39, and Zabula, A. V. et al., *Eur. J. Inorg. Chem.* 2008, pg. 5165.

In at least one embodiment, the metathesis catalyst is one or more of tricyclohexylphosphine[1,3-bis(2,4,6-trimethylphenyl)imidazol-2-ylidene][3-phenyl-1H-inden-1-ylidene]ruthenium(II) dichloride, tricyclohexylphosphine[3-phenyl-1H-inden-1-ylidene][1,3-bis(2,4,6-trimethylphenyl)-4,5-dihydro-imidazol-2-ylidene]ruthenium(II) dichloride, tricyclohexylphosphine[1,3-bis(2,4,6-trimethylphenyl)-4,5-dihydroimidazol-2-ylidene][(phenylthio)methylene]ruthenium(II) dichloride, bis(tricyclohexylphosphine)-3-phenyl-1H-inden-1-ylideneruthenium(II) dichloride, 1,3-bis(2,4,6-trimethylphenyl)-4,5-dihydroimidazol-2-ylidene [2-(i-propoxy)-5-(N,N-dimethylaminosulfonyl)phenyl] methyleneruthenium(II) dichloride, or [1,3-bis(2,4,6-trimethylphenyl)-2-imidazolidinylidene]-[2-[[(4-methylphenyl) imino]methyl]-4-nitrophenolyl]-[3-phenyl-1H-inden-1-ylidene]ruthenium(II) chloride.

In at least one embodiment, the catalyst is 1,3-bis(2,4,6-trimethylphenyl)-4,5-dihydroimidazol-2-ylidene[2-(i-propoxy)-5-(N,N-dimethylaminosulfonyl)phenyl]methyleneruthenium(II) dichloride and/or tricyclohexylphosphine[3-phenyl-1H-inden-1-ylidene][1,3-bis(2,4,6-trimethylphenyl)-4,5-dihydroimidazol-2-ylidene]ruthenium(II) dichloride.

In another embodiment, the metathesis catalyst is represented by Formula (VI) above, where: M is Os or Ru; $R^5$ is hydrogen; X and $X^1$ may be different or the same and are any anionic ligand; L and $L^1$ may be different or the same and are any neutral electron donor;

and $R^4$ may be hydrogen, substituted or unsubstituted alkyl, or substituted or unsubstituted aryl. $R^4$ can be hydrogen, $C_1$ to $C_{20}$ alkyl, or aryl. The $C_1$ to $C_{20}$ alkyl may optionally be substituted with one or more aryl, halide, hydroxy, $C_1$ to $C_{20}$ alkoxy, or $C_2$ to $C_{20}$ alkoxycarbonyl groups. The aryl may optionally be substituted with one or more $C_1$ to $C_{20}$ alkyl, aryl, hydroxyl, $C_1$ to $C_5$ alkoxy, amino, nitro, or halide groups. L and $L^1$ can be phosphines of the formula $PR^{3'}R^{4'}R^{5'}$, where $R^{3'}$ is a secondary alkyl or cycloalkyl, and $R^{4'}$ and $R^{5'}$ are aryl, $C_1$ to $C_{10}$ primary alkyl, secondary alkyl, or cycloalkyl. $R^{4'}$ and $R^{5'}$ may be the same or different. L and $L^1$ can be the same and are —P(cyclohexyl)$_3$, —P(cyclopentyl)$_3$, or —P(isopropyl)$_3$. X and $X^1$ can be the same and can be chlorine.

In another embodiment, the metathesis catalyst is a ruthenium and/or osmium carbene compound represented by the Formula (X):

Formula (X)

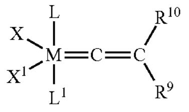

where M is Os or Ru, such as Ru; X, $X^1$, L, and $L^1$ are as described above for Formula (X); and $R^9$ and $R^{10}$ may be different or the same and may be hydrogen, substituted or unsubstituted alkyl, or substituted or unsubstituted aryl. The $R^9$ and $R^{10}$ groups may optionally include one or more of the following functional groups: alcohol, thiol, ketone, aldehyde, ester, ether, amine, imine, amide, nitro, carboxylic acid, disulfide, carbonate, isocyanate, carbodiimide, carboalkoxy, and halogen groups. Such compounds and their synthesis are described in, inter alia, U.S. Pat. No. 6,111,121.

In another embodiment, the metathesis catalyst useful herein may be any of the catalysts described in U.S. Pat. Nos. 6,111,121; 5,312,940; 5,342,909; 7,329,758; 5,831,108; 5,969,170; 6,759,537; 6,921,735; and US Patent Publication No. 2005-0261451 A1, including, but not limited to, benzylidene-bis(tricyclohexylphosphine)dichlororuthenium, benzylidene[1,3-bis(2,4,6-trimethylphenyl)-2 imidazolidinylidene]dichloro (tricyclohexyl phosphine) ruthenium, dichloro(o-isopropoxyphenylmethylene)(tricyclohexylphosphine)ruthenium(II), (1,3-bis-(2,4,6-trimethylphenyl)-2-imidazolidinylidene)dichloro(o-isopropoxyphenylmethylene)ruthenium, 1,3-bis(2-methylphenyl)-2-imidazolidinylidene]dichloro(2-isopropoxyphenylmethylene) ruthenium (II), [1,3-bis(2,4,6-trimethylphenyl)-2-imidazolidinylidene] dichloro[3-(2-pyridinyl)propylidene]ruthenium(II), [1,3-bis (2-methylphenyl)-2-imidazolidinylidene]dichloro(phenylmethylene) (tricyclohexylphosphine)ruthenium(II), [1,3-bis (2,4,6-trimethylphenyl)-2-imidazolidinylidene]dichloro(3-methyl-2-butenylidene) (tricyclohexylphosphine)ruthenium (II), and [1,3-bis(2,4,6-trimethylphenyl)-2-imidazolidinylidene]dichloro(benzylidene)bis(3-bromopyridine)ruthenium(II).

In another embodiment, the metathesis catalyst is represented by the formula (XI):

Formula (XI)

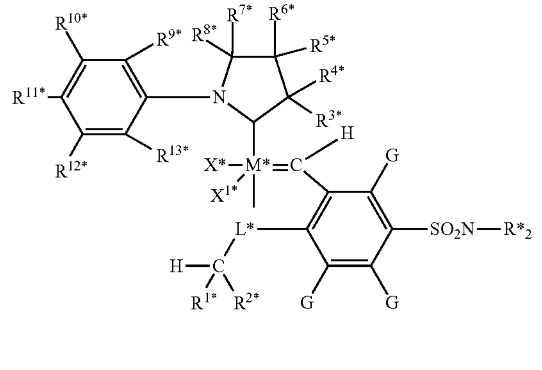

where

M* is a Group 8 metal, such as Ru or Os, such as Ru;

X* and $X^{1*}$ are, independently, any anionic ligand, such as a halogen (such as chlorine), an alkoxide or an alkyl sulfonate, or X* and $X^{1*}$ may be joined to form a dianionic group and may form a single ring of up to 30 non-hydrogen atoms or a multinuclear ring system of up to 30 non-hydrogen atoms;

L* is N—R, O, P—R, or S, such as N—R or O (R is a $C_1$ to $C_{30}$ hydrocarbyl or substituted hydrocarbyl, such as methyl, ethyl, propyl or butyl);

R* is hydrogen or a $C_1$ to $C_{30}$ hydrocarbyl or substituted hydrocarbyl, such as methyl;

$R^{1*}$, $R^{2*}$, $R^{3*}$, $R^{4*}$, $R^{5*}$, $R^{6*}$, $R^{7*}$, and $R^{8*}$ are, independently, hydrogen or a $C_1$ to $C_{30}$ hydrocarbyl or substituted hydrocarbyl, such as methyl, ethyl, propyl or butyl, such as $R^{1*}$, $R^{2*}$, $R^{3*}$, and $R^{4*}$ are methyl;

each $R^{9*}$ and $R^{13*}$ are, independently, hydrogen or a $C_1$ to $C_{30}$ hydrocarbyl or substituted hydrocarbyl, such as a $C_2$ to $C_6$ hydrocarbyl, such as ethyl;

$R^{10*}$, $R^{11*}$, $R^{12*}$ are, independently hydrogen or a $C_1$ to $C_{30}$ hydrocarbyl or substituted hydrocarbyl, such as hydrogen or methyl;

each G, is, independently, hydrogen, halogen or $C_1$ to $C_{30}$ substituted or unsubstituted hydrocarbyl (such as a $C_1$ to $C_{30}$ substituted or unsubstituted alkyl or a substituted or unsubstituted $C_4$ to $C_{30}$ aryl); and where any two adjacent R groups may form a single ring of up to 8 non-hydrogen atoms or a multinuclear ring system of up to 30 non-hydrogen atoms.

Any two adjacent R groups may form a fused ring having from 5 to 8 non-hydrogen atoms. The non-hydrogen atoms may be C and/or O. The adjacent R groups may form fused rings of 5 to 6 ring atoms, such as 5 to 6 carbon atoms. By adjacent is meant any two R groups located next to each other, for example $R^{3*}$ and $R^{4*}$ can form a ring and/or $R^{11*}$ and $R^{12*}$ can form a ring.

In at least one embodiment, the metathesis catalyst compound comprises one or more of:

2-(2,6-diethylphenyl)-3,5,5,5-tetramethylpyrrolidine[2-(i-propoxy)-5-(N,N-dimethylamino sulfonyl)phenyl]methylene ruthenium dichloride;

2-(mesityl)-3,3,5,5-tetramethylpyrrolidine[2-(i-propoxy)-5-(N,N-dimethylaminosulfonyl) phenyl]methylene ruthenium dichloride;

2-(2-isopropyl)-3,3,5,5-tetramethylpyrrolidine[2-(i-propoxy)-5-(N,N-dimethylaminosulfonyl) phenyl]methylene ruthenium dichloride;

2-(2,6-diethyl-4-fluorophenyl)-3,3,5,5-tetramethylpyrrolidine[2-(i-propoxy)-5-(N,N-dimethylaminosulfonyl)phenyl]methylene ruthenium dichloride; or mixtures thereof.

For further information on such metathesis catalysts, please see U.S. Ser. No. 12/939,054, filed Nov. 3, 2010, claiming priority to and the benefit of U.S. Ser. No. 61/259,514, filed Nov. 9, 2009. Many of the above named catalysts are generally available from Sigma-Aldrich Corp. (St. Louis, MO) or Strem Chemicals, Inc. (Newburyport, MA).

In at least one embodiment, a metathesis catalyst includes: a Group 8 metal complex represented by the Formula (XII):

(XII)

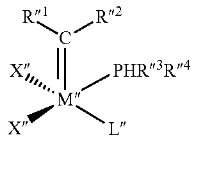

wherein

M" is a Group 8 metal (such as M is ruthenium or osmium, such as ruthenium);

each X" is independently an anionic ligand (such as selected from the group consisting of halides, alkoxides, aryloxides, and alkyl sulfonates, such as a halide, such as chloride);

$R''^1$ and $R''^2$ are independently selected from the group consisting of hydrogen, a $C_1$ to $C_{30}$ hydrocarbyl, and a $C_1$ to $C_{30}$ substituted hydrocarbyl (such as $R''^1$ and $R''^2$ are independently selected from the group consisting of methyl, ethyl, propyl, isopropyl, butyl, tert-butyl, sec-butyl, pentyl, cyclopentyl, hexyl, cyclohexyl, heptyl, octyl, cyclooctyl, and substituted analogs and isomers thereof, such as selected from the group consisting of tert-butyl, sec-butyl, cyclohexyl, and cyclooctyl);

$R''^3$ and $R''^4$ are independently selected from the group consisting of hydrogen, $C_1$ to $C_{12}$ hydrocarbyl groups, substituted $C_1$ to $C_{12}$ hydrocarbyl groups, and halides (such as $R''^3$ and $R''^4$ are independently selected from the group consisting of methyl, ethyl, propyl, isopropyl, butyl, tert-butyl, sec-butyl, pentyl, cyclopentyl, hexyl, cyclohexyl, heptyl, octyl, cyclooctyl, and substituted analogs and isomers thereof, such as selected from the group consisting of tert-butyl, sec-butyl, cyclohexyl, and cyclooctyl); and L" is a neutral donor ligand, such as L" is selected from the group consisting of a phosphine, a sulfonated phosphine, a phosphite, a phosphinite, a phosphonite, an arsine, a stibine, an ether, an amine, an imine, a sulfoxide, a carboxyl, a nitrosyl, a pyridine, a thioester, a cyclic carbene, and substituted analogs thereof; such as a phosphine, a sulfonated phosphine, an N-heterocyclic carbene, a cyclic alkyl amino carbene, and substituted analogs thereof (such as L" is selected from a phosphine, an N-heterocyclic carbene, a cyclic alkyl amino carbene, and substituted analogs thereof).

A "cyclic carbene" may be defined as a cyclic compound with a neutral dicoordinate carbon center featuring a lone pair of electrons. Such cyclic carbenes may be represented by the Formula (XIII) below:

(XIII)

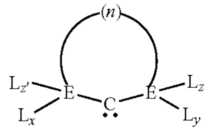

where n is a linking group comprising from one to four ring atoms selected from the group consisting of C, Si, N, P, O, and S, with available valences optionally occupied by H, oxo, hydrocarbyl, or substituted hydrocarbyl groups; such as n comprises two ring atoms of carbon with available valences occupied by H, oxo, hydrocarbyl or substituted hydrocarbyl groups; such as n is $C_2H_2$, $C_2H_4$, or substituted versions thereof;

each E is independently selected from the group comprising C, N, S, O, and P, with available valences optionally occupied by Lx, Ly, Lz, and Lz'; such as at least one E is a C; such as one E is a C and the other E is a N; such as both E's are C; and Lx, Ly, Lz, and Lz' are independently selected from the group comprising hydrogen, hydrocarbyl groups, and substituted hydrocarbyl groups; such as Lx, Ly, Lz, and Lz' are independently selected from the group comprising a hydrocarbyl group and substituted hydrocarbyl group having 1 to 40 carbon atoms; such as Lx, Ly, Lz, and Lz' are independently selected from the group comprising $C_{1-10}$ alkyl, substituted $C_{1-10}$ alkyl, $C_{2-10}$ alkenyl, substituted $C_{2-10}$ alkenyl, $C_{2-10}$ alkynyl, substituted $C_{2-10}$ alkynyl, aryl, and substituted aryl; such as Lx, Ly, Lz, and Lz' are independently selected from the group comprising methyl, ethyl, propyl, butyl (including isobutyl and n-butyl), pentyl, cyclopentyl, hexyl, cyclohexyl, octyl, cyclooctyl, nonyl, decyl, cyclodecyl, dodecyl, cyclododecyl, mesityl, adamantyl, phenyl, benzyl, tolulyl, chlorophenyl, 2,6-diethylphenyl, 2,6-diisopropylphenyl, 2-isopropylphenyl, 2-ethyl-6-methylphenyl, 3,5-ditertbutylphenyl, 2-tertbutylphenyl, and 2,3,4,5,6-pentamethylphenyl. Useful substituents include $C_{1-10}$ alkyl, $C_{2-10}$ alkenyl, $C_{2-10}$ alkynyl, aryl, $C_{1-10}$ alkoxy, $C_{2-10}$ alkenyloxy, $C_{2-10}$ alkynyloxy, aryloxy, $C_{2-10}$ alkoxycarbonyl, $C_{1-10}$ alkylthio, $C_{1-10}$ alkylsulfonyl, fluoro, chloro, bromo, iodo, oxo, amino, imine, nitrogen heterocycle, hydroxy, thiol, thiono, phosphorous, and carbene groups.

Examples of cyclic carbenes useful in embodiments include:

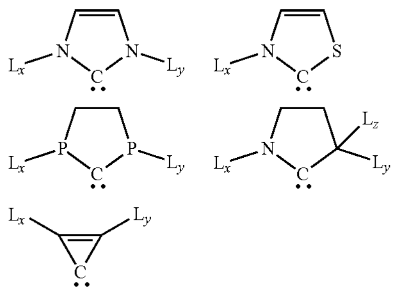

where Lx, Ly, and Lz are as defined above. In some embodiments, at least two of Lx, Ly, Lz, and Lz' may be joined to form a 3- to 12-membered spirocyclic ring, with available valences optionally occupied by H, oxo, halogens, hydrocarbyl or substituted hydrocarbyl groups. Useful substituents include $C_{1-10}$ alkyl, $C_{2-10}$ alkenyl, $C_{2-10}$ alkynyl, aryl, $C_{1-10}$ alkoxy, $C_{2-10}$ alkenyloxy, $C_{2-10}$ alkynyloxy, aryloxy, $C_{2-10}$ alkoxycarbonyl, $C_{1-10}$ alkylthio, $C_{1-10}$ alkylsulfonyl, fluoro, chloro, bromo, iodo, oxo, amino, imine, nitrogen heterocycle, hydroxy, thiol, thiono, phosphorous, and carbene groups.

Example cyclic carbenes include N-heterocyclic carbenes (NHCs). For purposes of the present disclosure, NHCs are cyclic carbenes of the types described in Formula (XIII) above, where each E is N and the available valences on the N are occupied by Lx and Ly. Example NHCs may be represented by the formula:

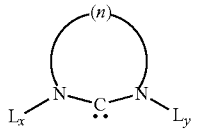

where n, Lx, and Ly are as described above in Formula (XIII)

Some particularly useful NHCs include:

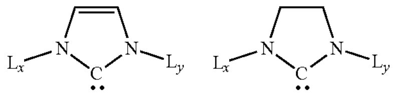

where Lx and Ly are as described above. Other useful NHCs include the compounds described in Hermann, W. A. Chem. Eur. J. 1996, 2, 772 and 1627; Enders, D. et al., *Angew. Chem. Int.* Ed. 1995, 34, 1021; Alder R. W., *Angew. Chem. Int. Ed.* 1996, 35, 1121; U.S. Ser. No. 61/314,388; and Bertrand, G. et al., *Chem. Rev.* 2000, 100, 39.

Example cyclic carbenes include cyclic alkyl amino carbenes (CAACs). In all embodiments herein, CAACs are cyclic carbenes of the types described in Formula (XIII) above, where one E is N and the other E is C, and the available valences on the N and C are occupied by Lx, Ly, and Lz. CAACs may be represented by the formula:

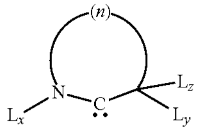

where n, Lx, Ly, and Lz are as described above in Formula (XIII).

Some particularly useful CAACs include:

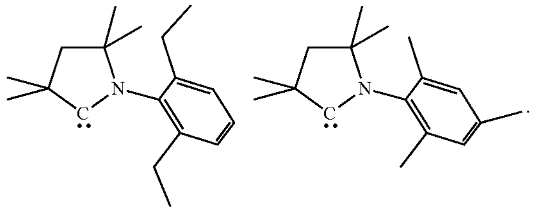

Other useful CAACs include the compounds described in U.S. Pat. No. 7,312,331; U.S. Ser. No. 61/259,514; and Bertrand et al, *Angew. Chem. Int. Ed.,* 2005, 44, 7236-7239.

Other carbenes useful in embodiments of the present disclosure include thiazolyidenes, P-heterocyclic carbenes (PHCs), and cyclopropenylidenes.

With respect to Group 8 metal complexes of Formula (XII), the phosphine ligands ($PHR''^3R''^4$) and L" are neutral donor ligands. In some embodiments, L" may be a phosphine having a formula $PHR''^5R''^6$. In such embodiments, the Group 8 metal complex may be represented by the Formula (XIV):

(XIV)

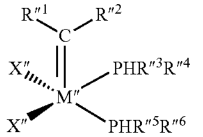

wherein

M" is a Group 8 metal (such as M is ruthenium or osmium, such as ruthenium);

each X" is independently an anionic ligand (such as selected from the group consisting of halides, alkoxides, aryloxides, and alkyl sulfonates, such as a halide, such as chloride);

R"[1] and R"[2] are independently selected from the group consisting of hydrogen, a $C_1$ to $C_{30}$ hydrocarbyl, and a $C_1$ to $C_{30}$ substituted hydrocarbyl (such as R"[1] and R"[2] are independently selected from the group consisting of methyl, ethyl, propyl, isopropyl, butyl, tert-butyl, sec-butyl, pentyl, cyclopentyl, hexyl, cyclohexyl, heptyl, octyl, cyclooctyl, and substituted analogs and isomers thereof, such as selected from the group consisting of tert-butyl, sec-butyl, cyclohexyl, and cyclooctyl); and R"[3], R"[4], R"[5], and R"[6] are independently selected from the group consisting of hydrogen, $C_1$ to $C_{12}$ hydrocarbyl groups, substituted $C_1$ to $C_{12}$ hydrocarbyl groups, and halides (such as R"[3], R"[4], R"[5], and R"[6] are independently selected from the group consisting of methyl, ethyl, propyl, isopropyl, butyl, tert-butyl, sec-butyl, pentyl, cyclopentyl, hexyl, cyclohexyl, heptyl, octyl, cyclooctyl, and substituted analogs and isomers thereof, such as selected from the group consisting of tert-butyl, sec-butyl, cyclohexyl, and cyclooctyl).

With respect to embodiments where L" is a phosphine having a formula PHR"[5]R"[6], in some embodiments, at least one phosphine ligand is a secondary phosphine ligand. In such embodiments, where at least one of the neutral donor ligands is a secondary phosphine ligand, R"[3] and R"[4] or R"[5] and R"[6] are selected from the group consisting of $C_1$ to $C_{12}$ hydrocarbyl groups, substituted $C_1$ to $C_{12}$ hydrocarbyl groups, and halides. In particular embodiments, both donor ligands are secondary phosphine ligands and R"[3], R"[4], R"[5], and R"[6] are selected from the group consisting of $C_1$ to $C_{12}$ hydrocarbyl groups, substituted $C_1$ to $C_{12}$ hydrocarbyl groups, and halides.

With respect to embodiments where L" is a phosphine having a formula PHR"[5]R"[6], in particular embodiments, at least one donor ligand is a primary phosphine ligand. In such embodiments where at least one of the phosphine ligands is a primary phosphine ligand, one of R"[3] and R"[4] or one of R"[5] and R"[6] is selected from the group consisting of $C_1$ to $C_{12}$ hydrocarbyl groups, substituted $C_1$ to $C_{12}$ hydrocarbyl groups, and halides. In particular embodiments, both donor ligands are primary phosphine ligands and one of R"[3] and R"[4] and one of R"[5] and R"[6] is selected from the group consisting of $C_1$ to $C_{12}$ hydrocarbyl groups, substituted $C_1$ to $C_{12}$ hydrocarbyl groups, and halides.

In some embodiments, R"[3] and R"[4] form a ring. With respect to embodiments where L" is a phosphine having a formula PHR"[5]R"[6], in particular embodiments, R"[5] and R"[6] form a ring. In yet other embodiments, R"[3] and R"[4] form a ring and R"[5] and R"[6] form a ring. In other embodiments, R"[3] and at least one of R"[5] and R"[6] may form a ring, thereby forming a chelating phosphine ligand. In other embodiments, R"[4] and at least one of R"[5] and R"[6] may form a ring, thereby forming a chelating phosphine ligand.

In particular embodiments, the Group 8 metal complex is selected from:

$[(HP(tert\text{-}butyl)_2)_2Ru(C_5H_8)Cl_2]$,
$[(H_2P(tert\text{-}butyl))_2Ru(C_5H_8)Cl_2]$,
$[(HP(cyclohexyl)_2)_2Ru(C_5H_8)Cl_2]$,
$[(H_2P(cyclohexyl))_2Ru(C_5H_8)Cl_2]$,
$[(HP(cyclopentyl)_2)_2Ru(C_5H_8)Cl_2]$,
$[(H_2P(cyclopentyl))_2Ru(C_5H_8)Cl_2]$,
$[(HP(n\text{-}butyl)_2)_2Ru(C_5H_8)Cl_2]$,
$[(H_2P(n\text{-}butyl))_2Ru(C_5H_8)Cl_2]$,
$[(HP(sec\text{-}butyl)_2)_2Ru(C_5H_8)Cl_2]$,
$[(H_2P(sec\text{-}butyl))_2Ru(C_5H_8)Cl_2]$, and fluoride and bromide derivatives thereof (such as wherein the $Cl_2$ in the above list is replaced with $F_2$, $Br_2$, ClF, ClBr or FBr).

In some embodiments, the metathesis catalyst may be selected from those described in U.S. Pat. Nos. 8,329,921; 8,519,147; US 2011/0112349; U.S. Pat. Nos. 8,809,563; 9,024,034; 8,557,902; US 2012/0077945; U.S. Pat. Nos. 8,524,930; 9,181,360; 8,623,962; 8,063,232; 8,604,148; and 9,714,393.

In certain embodiments, the catalyst employed in the process of the present disclosure may be bound to or deposited onto a solid support. In particular, the metathesis catalyst may be bound to or deposited onto a solid support, which may simplify catalyst recovery. In addition, the support may increase catalyst strength and attrition resistance. Suitable catalyst supports include, without limitation, silicas; aluminas; silica-aluminas; aluminosilicates, including zeolites and other crystalline porous aluminosilicates; as well as titanias; zirconia; magnesium oxide; carbon; and cross-linked polymeric resins, such as functionalized cross-linked polystyrenes, e.g., chloromethyl-functionalized cross-linked polystyrenes; such as silica or alumina. The metathesis catalyst may be deposited onto the support by any method known to those skilled in the art, including, for example, impregnation, ion-exchange, deposition-precipitation, and vapor deposition. Alternatively, a component of the catalyst, such as the metathesis catalyst, may be chemically bound to the support via one or more covalent chemical bonds, for example, the catalyst may be immobilized by one or more covalent bonds with one or more of substituents of a ligand of the metathesis catalyst. For example, the metathesis catalyst may be deposited onto a silica support. Further, the metathesis catalyst may be preloaded onto the solid support before forming the catalyst. Alternatively, the supported catalyst may be generated in situ.

If a catalyst support is used, the catalyst compound may be loaded onto the catalyst support in any amount, provided that the metathesis process of the present disclosure proceeds to the metathesis products. Generally, the catalyst compound is loaded onto the support in an amount based on the weight of the transition metal, such as the Group 8 metal, such as ruthenium or osmium, relative to the total weight of the catalysts plus support. The catalyst compound may be loaded onto the support in an amount greater than about 0.01 wt % of the Group 8 metal, based upon the weight of the catalysts plus support and such as greater than about 0.05 wt % of the Group 8 metal. Generally, the catalyst compound is loaded onto the support in an amount that is less than about 20 wt % of the Group 8 metal, and such as less than about 10 wt % of the Group 8 metal.

In embodiments where the catalyst compound utilized in a method of the present disclosure is bound to or deposited on a solid catalyst support, the solid catalyst support will render the catalyst compound heterogeneous.

In certain embodiments, the catalyst employed in the process of the present disclosure is metal-oxide based heterogeneous catalyst. In particular, the metathesis catalyst may be $WO_3/Al_2O_3$, $MoO_3/Al_2O_3$, $WO_3/SiO_2$, $MoO_3/SiO_2$, supported $Re_2O_7$, or a combination thereof.

Isomerization Catalysts

As mentioned above, an isomerization catalyst can be used in addition to the ring closing metathesis catalyst. Isomerization catalysts may include RCM catalysts, such as ruthenium-based catalysts, their decomposed forms featuring Ru-hydride moieties and/or ruthenium metal species, such as nanoparticles. The isomerization role of metathetically active ruthenium compounds and products of their decomposition or deactivation is described in Fogg, D. E. et al., *ChemCatChem,* 2016, 8, 2446 (Catalyst Decomposition during Olefin Metathesis Yields Isomerization-Active Ruthenium Nanoparticles) and Jensen, V. R., *J Am. Chem. Soc.,* 2017, 139, 16609 (Loss and Reformation of Ruthenium Alkylidene: Connecting Olefin Metathesis, Catalyst Deactivation, Regeneration, and Isomerization), Grela, K. et al., *Chem. Eur. J.,* 2018, 24, 10403 (Sequential Alkene Isomerization and Ring-Closing Metathesis in Production of Macrocyclic Musks from Biomass).

The isomerization catalysts may also be well-defined metal complexes, such as metal hydrides supported by organic ligand frameworks or the complexes where active hydride species are generated in situ.

The isomerization catalysts may be heterogeneous catalysts, such as solid acid catalysts or metal hydrides.

In at least one embodiment, an isomerization catalyst is selected from:

$[Fe(CO)_{5]}$,
$[Fe_3(CO)_{12}]$,
$[RhCl(PPh_3)_3]$,
$[Pd(NCPh)_2Cl_2]$,
$[HRuCl(PPh_3)_3]$,
$[HNi(PPh_3)_3]Cl$,
$[HNi(PCy_3)_2Cl]$,
$[HCo(CO)_4]$,
Tricyclohexylphosphine[1,3-bis(2,4,6-trimethylphenyl)imidazol-2-ylidene][3-phenyl-1H-inden-1-ylidene]ruthenium(II) dichloride,
or combination(s) thereof.

Cyclic Olefin Products

Cyclic olefin products of the present disclosure can include substituted or unsubstituted cyclic olefins selected from $C_5$-$C_{50}$ cyclic olefins, such as $C_5$-$C_{40}$ cyclic olefins, such as $C_5$-$C_{30}$ cyclic olefins, such as $C_5$-$C_{20}$ cyclic olefins, such as $C_6$-$C_{15}$ cyclic olefins, such as $C_6$-$C_{10}$ cyclic olefins, such as $C_7$-$C_9$ cyclic olefins, alternatively $C_5$-$C_7$ cyclic olefins. Cyclic olefins of the present disclosure can monoolefins, diolefins, or triolefins. In at least one embodiment, a cyclic olefin is a monoolefin.

In some embodiments, a cyclic olefin is a monoolefin selected from cyclopentene, cyclohexene, cycloheptene, cyclooctene, cyclononene, cyclodecene, cycloundecene, cyclododecene, cyclotridecene, cyclotetradecene, cyclopentadecene, cyclohexadecene, cycloheptadecene, cyclooctadecene, cyclononadecene, cycloicosene, cycloheneicosene, cyclodocosene, cyclotricosene, cyclotetracosene, cyclopentacosene, cyclohexacosene, cycloheptacosene, cyclooctacosene, cyclononacosene, cyclotriacontene, methyl-containing derivatives thereof, ethyl-containing derivatives thereof, vinyl- or vinylidene-containing derivatives thereof, and combination(s) thereof.

In some embodiments, a cyclic olefin is a diolefin selected from cyclopentadiene, cyclohexadiene, cycloheptadiene, cyclooctadiene, cyclononadiene, cyclodecadiene, cycloundecadiene, cyclododecadiene, cyclotridecadiene, cyclotetradecadiene, cyclopentadecadiene, cyclohexadecadiene, cycloheptadecadiene, cyclooctadecadiene, cyclononadecadiene, cycloicosadiene, cycloheneicosadiene, cyclodocosadiene, cyclotricosadiene, cyclotetracosadiene, cyclopentacosadiene, cyclohexacosadiene, cycloheptacosadiene, cyclooctacosadiene, cyclononacosadiene, cyclotriacontadiene, methyl-containing derivatives thereof, ethyl-containing derivatives thereof, vinyl- or vinylidene-containing derivatives thereof, and combination(s) thereof, and combination(s) thereof.

For high yielded processes of the present disclosure, a product formed can be a mixture of cyclic olefin(s), optionally some saturated cycloalkanes, optionally some linear olefins, and optionally some saturated alkanes. In some embodiments, a product has a linear olefin content, based on the weight of the product, of less than about 10 wt %, such as less than about 5 wt %, such as less than about 2 wt %, such as less than about 1 wt %, such as less than about 0.5 wt %, such as less than about 0.1 wt %, such as 0 wt %. For example, a product can have a linear olefin content of about 0.1 wt % to about 10 wt %, such as about 0.1 wt % to about 5 wt %, such as about 0.1 wt % to about 1 wt %, such as about 0.1 wt % to about 0.5 wt %, such 0 wt %. In some embodiments, a product has a saturated cycloalkane content, based on the weight of the product, of less than about 10 wt %, such as less than about 5 wt %, such as less than about 2 wt %, such as less than about 1 wt %, such as less than about 0.5 wt %, such as less than about 0.1 wt %, such as 0 wt %. For example, a product can have a saturated cycloalkane content of about 0.1 wt % to about 10 wt %, such as about 0.1 wt % to about 5 wt %, such as about 0.1 wt % to about 1 wt %, such as about 0.1 wt % to about 0.5 wt %, such 0 wt %. In some embodiments, a product has a saturated linear alkane content, based on the weight of the product, of less than about 10 wt %, such as less than about 5 wt %, such as less than about 2 wt %, such as less than about 1 wt %, such as less than about 0.5 wt %, such as less than about 0.1 wt %, such as 0 wt %. For example, a product can have a saturated linear alkane content of about 0.1 wt % to about 10 wt %, such as about 0.1 wt % to about 5 wt %, such as about 0.1 wt % to about 1 wt %, such as about 0.1 wt % to about 0.5 wt %, such 0 wt %.

In some embodiments, processes of the present disclosure can provide cyclic olefins having a purity (e.g., cyclic olefin content), as determined by Gas Chromatography (GC), of greater than 90%, such as greater than 95%, such as greater than 98%, such as greater than 99%, such as greater than 99.9%, such as from about 90% to about 99.99%, such as from about 95% to about 99.99%, such as 98% to 99.99%, such as 99% to 99.99%. For example, in some embodiments, cyclic olefin products of the present disclosure can have a cyclic olefin content, based on the weight of the cyclic olefin product, as determined by GC, of greater than 90 wt %, such as greater than 95 wt %, such as greater than 98 wt %, such as greater than 99 wt %, such as greater than 99.9 wt %, such as from about 90 wt % to about 99.99 wt %, such as from about 95 wt % to about 99.99 wt %, such as 98 wt % to 99.99 wt %, such as 99 wt % to 99.99 wt %. Advantageously, high purity of cyclic olefins of the present disclosure can be achieved as a reactor effluent without a need for purification steps (such as distillation). In addition, the high yield of high purity cyclic olefins reduces or eliminates the presence of byproducts having similar or the same boiling point as the desired cyclic olefin(s). For example, distillation of linear olefins from cyclic olefins would otherwise result in a significant loss in the amount of pure cyclic olefin (Register, R. A., *ACS Macro Letters,* 2017, 6, 112). Side products of conventional manufacturing of cyclopentene by selective hydrogenation of cyclopentadiene, 1,3-pentadienes (cis/trans), have a boiling point (42° C.) close to that in cyclopentene (44° C.), which makes the separation of cyclopentene from these contaminations challenging even at the industrial scale. Non-cyclic olefin contaminations in cyclic olefins serve as chain transfer agents in ROMP thus reducing molecular weights of the resulting polymer products.

De-Polymerization Examples

Solid linear and cured polypentenamers were selectively depolymerized into pure cyclopentene upon mechanical mixing with a solid RCM catalyst (Grubbs 2nd generation, 0.05 mol %). No special pretreatment of polypentenamer samples were conducted prior depolymerization. The yield of reclaimed cyclopentene was 75-93%. Interestingly, the sulfur bridging units in the cured sample did not substantially mitigate the activity of the RCM catalyst. Thus, polypentenamer based tires can be recycled back to monomers in high yields.

The purity of the recycled monomer was found to be about 99.5+% by $^{1}$H NMR spectroscopy and GC analysis. The corresponding polymerization-depolymerization cycle can be used for purifying cyclopentene from contaminants including straight olefins.

For purposes herein, the purity of recycled monomer can be monitored and estimated with $^{1}$H NMR method using a Bruker 400 MHz instrument, as indicated. Pulse program zgcw30 can be used with $D_1$=60 s and ns=2 or 4. $CDCl_3$ can be the lock solvent. The chemical shift of cyclopentene monomer double bond protons is about 5.75 ppm and the chemical shift of polypentenamer double bond protons is about 5.53 ppm.

Gas chromatography (GC) was performed using an Agilent 6890A instrument with split inlet, flame ionization detector (GC-FID) with helium carrier and a Petrocol DH 150 m×0.25 mm×1 µm (MilliporeSigma, USA) with a 100% polydimethyl siloxane phase. The parameters of the GC method includes: 1) Injector: 0.1 uL; 2) Inlet: 250 C, 20:1 Split, 80 psi, He; 3) Oven: 60° C. (hold 2 min) to 100° C. at 4 C/min to 300° C. at 15 C/min (hold 15 min); 4) Column: Ramped pressure 80 psi (hold 12 min) to 100 psi at 3 psi/min, initial flow 3.3 mL/min; 5) Detector: 270° C., $H_2$ flow 40 mL/min, Air flow 450 mL/min, Make up+Column flow 30 mL/min.

Depolymerization of Natural and Synthetic Rubbers

The strategy for the recycling of cyclic olefins from natural or synthetic rubbers included the application of a catalyst system(s) with active isomerization and ring-closing metathesis capability, such as a ruthenium based system. As shown in Scheme 1 previously, in the first reaction step the isomerization in polyisoprene gave a structural unit where four single C—C bonds are separated by double bonds. Then, the following ring-closing metathesis reaction for the resulting fragment gives methyl-branched cyclopentene. Subsequent isomerization/RCM cycles can further depolymerize a rubber material with the formation of unsaturated of $C_5$ cyclics and a conjugated polymer.

Preparation of Polypentenamers

Sample 1. Typical procedure for preparation of polypentenamer samples: The catalyst was formed in situ by adding solid $(p\text{-}MeC_6H_4O)_2AlCl$ (202 mg, 0.731 mmol) to a solution of $WCl_6$ (145 mg, 0.366 mmol) in toluene (10 mL). After stirring for one hour, the resulting mixture was added to the solution of cyclopentene (99.7 g, 1.464 mol) and triethylaluminum (84 mg, 0.732 mmol) in toluene (600 mL) at 0° C. After 75 min of intense mechanical stirring, a solution of 2,6-di-tert-butyl-4-methylphenol (1.00 g, 4.48 mmol) in 100 mL of ethanol/toluene mixture (1:4, v:v, respectively) was added. The obtained mixture was poured into ethanol (2 L). The precipitated polymer was then washed 3 times with ethanol (250 mL each) and dried under vacuum at 50° C. for 4 hours to give 50.7 g of the polymeric product.

Sample 2. The catalyst was formed in situ by adding solid $(4\text{-}(PhCH_2)C_6H_4O)_2AlCl$ (314 mg, 0.731 mmol) to a solution of $WCl_6$ (145 mg, 0.366 mmol) in toluene (10 mL). After stirring for one hour at ambient conditions, the resulting mixture was added to a solution containing cyclopentene (first comonomer) (99.6 g, 1.463 mol), triethylaluminum (activator) (83 mg, 0.731 mmol), and toluene (600 mL) at 3° C. A solution of dicyclopentadiene (DCPD) (second comonomer) (1.934 g, 15 mmol) in toluene (64 mL) was slowly added to the reaction mixture over 60 minutes under intense mechanical stirring. After additional 2 hours, a solution of 2,6-di-tert-butyl-4-methylphenol (1.00 g, 4.48 mmol) in 100 mL of ethanol/toluene mixture (1:4, v:v, respectively) was added. The obtained mixture was added to methanol (4 L). The precipitated polymer was washed 3 times with methanol (500 mL each) and dried under vacuum at 55° C. for 4 hours to give 55.4 g of the product containing 1.8 mol % of incorporated DCPD according to $^{1}$H NMR spectroscopy (Dragutan et. al. Green Metathesis Chemistry: Great Challenges in Synthesis, Catalysis, and Nanotechnology (2010), 369-380).

Depolymerization of Polypentenamer

Example 1. Hoveyda-Grubbs catalyst (2nd generation) was used (also referred to as (1,3-bis-(2,4,6,-trimethylphenyl)-2-imidazolidinylidene)dichloro(o-isopropoxyphenylmethylene)ruthenium). A solution of Hoveyda-Grubbs catalyst (2nd generation, 15 mg, 0.03 mol %) in 1 mL of toluene was added to solid polypentenamer (Sample 1) in a 100 mL flask. The resulting mixture was stirred at 55-85° C. under vacuum in a completely closed system cooled by a liquid nitrogen compartment for collecting volatile depolymerization products. After 2 hour, the depolymerization reaction was visually completed yielding ca 5.60 g of a colorless liquid containing cyclopentene (4.70 g) and toluene (0.90 g) according to $^{1}$H NMR spectroscopy. Total monomer recovery: 75%.

Example 2. Solid Hoveyda-Grubbs catalyst (2nd Generation, 30 mg, 0.007 mol %) was added to the 1 L 2-necked flask, equipped with a mechanical stirrer and an outlet for removal and subsequent condensation of volatile depolymerization products at −196° C., and containing 50 g of polypentenamer Sample 1. Depolymerization under stirring (60-200 rmp) in vacuo at 70-80° C. resulted in almost complete disappearance of the polymer in 4 hours. The monomer was recovered in the yield of 46.1 g (92%).

Example 3. Solid Hoveyda-Grubbs catalyst (2nd Generation, 30 mg) was added to the 1 L 2-necked flask equipped with a mechanical stirrer and an outlet for removal and subsequent condensation of volatile depolymerization products at −196° C. and containing 73 g of polypentenamer Sample 1. Depolymerization was performed under stirring (60-200 rmp) in vacuo at 75° C. Upon depolymerizing of polymer to ca ¼ of its original volume, a fresh portion of polypentenamer was added. Totally, 3 subsequent additions were performed (61 g, 46 g and 27 g) to give 154 g of cyclopentene. Yield: 74.4%.

Control Example 4. Polypentenamer Sample 1 (2 g) was heated up (70-80° C.) in vacuo for 3 hours under stirring in the absence of ruthenium catalyst. No depolymerization was observed. These results show that the ROMP catalyst residues are metathetically non-active under those conditions and observed depolymerization in previous Examples was induced by ruthenium-based catalysts only.

Example 5. Cyclopentene obtained in Examples 2 and 3 was combined and distilled. Three fractions were collected: 1st fraction with the boiling point up to 44° C., ca 4 g; 2nd fraction with the boiling point 44-45° C., 160.8 g; and 3rd fraction with the boiling point 45-50° C., 7.5 g. The GC compositions of all three fractions and crude cyclopentene are to summarized in Table 3.

TABLE 3

GC composition for the fractions obtained in Example 5.

| Component | Fraction 1 bp < 44° C. | Fraction 2 bp 44-45° C. | Fraction 3 bp 45-50° C. |
|---|---|---|---|
| Propane/butane | 0.003 | | |
| Propane/butane | 0.002 | 0.002 | |
| Butane | 0.004 | 0.006 | |
| Butene | 0.037 | | |
| 3-Methyl-1-butene | 0.003 | | |
| 1-Pentene | 0.211 | 0.109 | 0.020 |
| n-Pentane | 0.002 | 0.002 | |
| Cyclopentadiene | | 0.003 | 0.002 |
| Cyclopentene | 98.620 | 97.329 | 97.153 |
| Cyclopentane | | | 0.004 |
| Hexene | | | 0.012 |
| Hexane | | | 0.017 |
| Isoheptane | | 0.005 | |
| Heptane | | 0.013 | 0.003 |
| Methylcyclopentene | | | 0.006 |
| Cyclohexadiene | | | 0.010 |
| Heptadiene | 0.006 | 0.018 | 0.029 |
| Cyclohexene | 0.032 | 0.085 | 0.159 |
| Heptene | | | 0.003 |
| $C_5$ oxygenate | 0.009 | | |
| Toluene | 0.714 | 2.378 | 2.551 |
| $C_5$ oxygenate | 0.009 | | |
| Octene | | 0.004 | 0.005 |
| 2-cyclopentenone | 0.223 | | |
| 1,6-cyclodecadiene | 0.037 | 0.038 | 0.023 |

Example 6. Solid Hoveyda-Grubbs catalyst (2nd Generation, 50 mg), polypentenamer Sample 1 (140 g) and 4 mL of SpectraSyn4 (a poly alpha-olefin synthetic base stock commercially available from ExxonMobil Corporation) were added to a 1 L 3-necked flask equipped with a mechanical stirrer and a vacuum condenser cooled by liquid nitrogen. Depolymerization was performed under stirring (60-200 rmp) in vacuo at 75° C. Upon depolymerizing of polymer to ca ¼ of its original volume, a new portion of polypentenamer Sample 1 was added. Totally, 2 subsequent additions were performed (135 g and 55 g, 330 g totally) to give 305 g of crude recovered cyclopentene over 4 hours (yield 92.4%). Distillation afforded 275 g of pure cyclopentene (purity 99.8%, GC). Major components of remaining, undistilled product (30 g) were cyclopentene (92.7%) and cyclohexene (3.85%). Cyclohexene and higher cyclic olefins were formed upon isomerization and subsequent RCM of polypentenamer. The GC compositions of the products, obtained in Example 6 are summarized in Table 4. Overall cyclopentene recovery yield: 302 g (91.6%)

TABLE 4

GC composition for the product obtained in Example 6.

| Component | Area, % distilled product | Area, % remaining product |
|---|---|---|
| 3-Methyl-1-butene | 0.007 | 0.007 |
| Isopentane | 0.001 | 0.000 |
| 1-Pentene | 0.018 | 0.001 |

TABLE 4-continued

GC composition for the product obtained in Example 6.

| Component | Area, % distilled product | Area, % remaining product |
|---|---|---|
| n-Pentane | 0.001 | 0.000 |
| Isoprene/trans-2-Pentene | 0.001 | 0.000 |
| Cis-2-pentene | 0.001 | 0.000 |
| cyclopentadiene | 0.001 | 0.001 |
| Cyclopentene | 99.806 | 92.743 |
| Cyclohexene | 0.119 | 3.849 |
| Cyclohexadiene | 0.005 | 0.253 |
| Toluene | 0.017 | 0.618 |
| Cycloheptene | 0.004 | 0.748 |
| Cycloheptadiene | 0.001 | 0.189 |
| 2-Cyclohexe-1-one | 0.000 | 0.045 |
| 2-Cyclohexene-1-ol | 0.000 | 0.059 |
| Dicyclopentadiene | 0.000 | 0.002 |
| 1,6-Cyclodecadiene | 0.000 | 0.123 |
| $C_{12}H_{18}$ | 0.000 | 0.422 |
| 2,6-Di-tert-butyl-4-methylphenol | 0.000 | 0.186 |
| Unidentified products | 0.017 | 0.754 |

Depolymerization of Cyclopentene-DCPD Copolymer

Example 7. Cyclopentene-dicyclopentadiene copolymer Sample 2 (53 g, cis/trans 18/82%, 1.9 mol % DCPD) was depolymerized using Hoveyda-Grubbs catalyst (2nd Generation, 45 mg). The 1 L flask, equipped with a magnetic stirrer was charged with the copolymer, SpectraSyn4 (5 mL) and attached to a receiving flask over an adaptor arm. The system was evacuated before cooling the receiving flask with liquid nitrogen. Depolymerization was performed at 75° C. under static vacuum. Complete disappearance of the polymer was observed in 3 hours. Around 49 g of cyclopentene were obtained. Recovery yield: 96%. The GC compositions of the product is summarized in Table 5.

TABLE 5

GC composition for the product obtained in Example 7.

| Component | Area % |
|---|---|
| 3-Methyl-1-butene | 0.008 |
| 1-Pentene | 0.011 |
| Cyclopentadiene | 0.001 |
| Cyclopentene | 98.620 |
| Cyclohexene | 0.133 |
| Toluene | 0.838 |
| 2,6-Di-tert-butyl-4-methylphenol | 0.054 |
| Unidentified products | 0.336 |

TABLE 6

| Summary of Depolymerization Experiments. | | | | | |
|---|---|---|---|---|---|
| | Monomer recovery, mol % | Temperature, ° C. | Catalyst | Catalyst activity, g-cyclic olefin/g-Ru | Catalyst activity, g-cyclic olefin/g-Ru/hour |
| Example 1 | 75 | 55-85 | Grubbs (2nd generation) | 1303 | 651 |
| Example 2 | 92 | 70-80 | Hoveyda-Grubbs (2nd generation) | 9544 | 2386 |
| Example 3 | 74.4 | 75 | Hoveyda-Grubbs (2nd generation) | 31884 | 7971 |
| Example 6 | 91.6 | 75 | Hoveyda-Grubbs (2nd generation) | 37515 | 9379 |
| Example 7 | 96 | 75 | Hoveyda-Grubbs (2nd generation) | 6473 | 2158 |

Cured Polypentenamers

Example 8. Vulcanized/cured polypentenamer sample was prepared in two steps. First, the components listed in Table 7 were mechanically mixed at 80° C. using an internal (Brabender™) mixer. The compounds were then molded into plaques with thickness=0.5 mm and cured at 160° C. for 25 minutes using a hot press. FIG. 1 is a graph illustrating vulcanization (cure kinetics) curve for the polypentenamer sample measured at 160° C. Dotted lines indicates 100% and 90% cure state. The curing time was enough for 90% cure state of the sample, according to the vulcanization curve data measured in an ARES G2 rheometer (TA Instruments™), and shown in FIG. 1. (In FIG. 1, the top most solid line is G* vs. time, and the lower solid line is the temperature vs. time).

TABLE 7

| Recipe for polypentenamer vulcanization. | |
|---|---|
| Ingredient | phr |
| polypentenamer Sample 1 | 100 |
| Zinc stearate (Sigma-Aldrich, technical grade) | 0.5 |
| Diphenylguanidine (DPG) (98 + %, TCI) | 0.2 |
| N-Cyclohexyl-2-benzothiazole sulfenamide (CBS) (98 + %, TCI) | 0.2 |
| Sulfur (99.5%, AkroChem) | 0.5 |

Examples 9-11. Second, vulcanized/cured polypentenamer and blends of polypentenamer with polybutadiene and natural rubber were prepared using a representative truck and bus formulation shown in Table 8. A two stage mixing process, involving a 1st and 2nd pass non-productive mix and a 3rd pass productive mix, was carried out on an Intelli-Torque brabender on a 66 gram basis. The 1st non-productive pass initial conditions were 35 RPMs (round-per-minute) and 75° C. for the initial addition of the polymer or polymers. Once the polymer was added to the mixing head, RPMs were increased to 50, after which half the carbon black loading was added over two minutes of mixing, followed by addition of antioxidant, ZnO, stearic acid, and wax over 30 seconds, followed by the second half of the carbon black loading over 2 minutes. After the second half of the carbon black loading was added, RPMs were increased to 100 and the mixture was allowed to mix for 8 minutes or until a mixture achieved the temperature of 150° C., whichever came first. Then, the polymer mixture was removed ("dumped") from the brabender and cold pressed. The 2nd non-productive pass involves an initial brabender condition of 35 RPM and 75° C. Over the 30 seconds the productive mix from the 1st pass was added back into the brabender. Once added, the RPMs were increased to 100 and the polymer mixture was allowed to mix for 3 minutes or until the polymer mixture reached a temperature of 150° C., after which the mixture was "dumped" and cold pressed. Here the amount of polymer mixture added is denoted as the non-productive master batch. The 3rd pass productive mix involved an initial brabender setting of 35 RPM and 75° C. The polymer mixture was added over the course of 30 seconds, then the remaining cure package components were added to the polymer mixture in the brabender over the course of 1.5 minutes. After the cure package was added, the RPMs were increased to 50 and allowed to mix for 3 minutes. The RPMs were adjusted to keep the mixing temperature below 100° C. After three minutes the polymer mixture was dumped and cold pressed. The polymer mixture cure kinetics were then determined on a Rubber Process Analyzer (RPA) at 160° C., 1 Hz, and 0.1% strain for 60 minutes. The t90, the time it takes for the torque to increase to 90% of the maximum torque plateau, was determine as defined in ASTM 5289. The polymer mixture was then cured into a mold to its t90 plus 5 minutes at 160° C. and then used for depolymerization experiments.

Examples 9-11 were dried in a vacuum oven at 55° C. at least 4 hours before depolymerization experiments.

TABLE 8

| Recipe for polypentenamer blends vulcanization. | | | |
|---|---|---|---|
| | Example 9 | Example 10 | Example 11 |
| SIR CV 60 | 0 | 0 | 70 |
| Budene 1208 | 0 | 30 | 0 |
| Polypentenamer Sample 1 | 100 | 70 | 30 |
| Carbon black N234 | 55 | 55 | 55 |
| Zinc Bar | 3 | 3 | 3 |
| Stearic Acid (Akrochem) | 3 | 3 | 3 |
| Santoflex 6PPD (antioxidant) | 2 | 2 | 2 |
| Paraffinic wax | 1 | 1 | 1 |
| Total (phr): | 164 | 164 | 164 |
| Non-Productive Master batch | 164 | 164 | 164 |
| N-(cyclohexylthio) phthalimide (CTP, Akrochem) | 0.2 | 0.2 | 0.2 |

TABLE 8-continued

| Recipe for polypentenamer blends vulcanization. | | | |
|---|---|---|---|
| | Example 9 | Example 10 | Example 11 |
| N-cyclohexyl-2-benzothiazolesulfenamide (CBS, Vanderbilt Chemicals) | 1.6 | 1.6 | 1.6 |
| DPG | 0 | 0 | 0 |
| Sulfur | 1.4 | 1.4 | 1.4 |
| Total (phr): | 167.2 | 167.2 | 167.2 |

Depolymerization of Cured Polypentenamer

Figure 2:
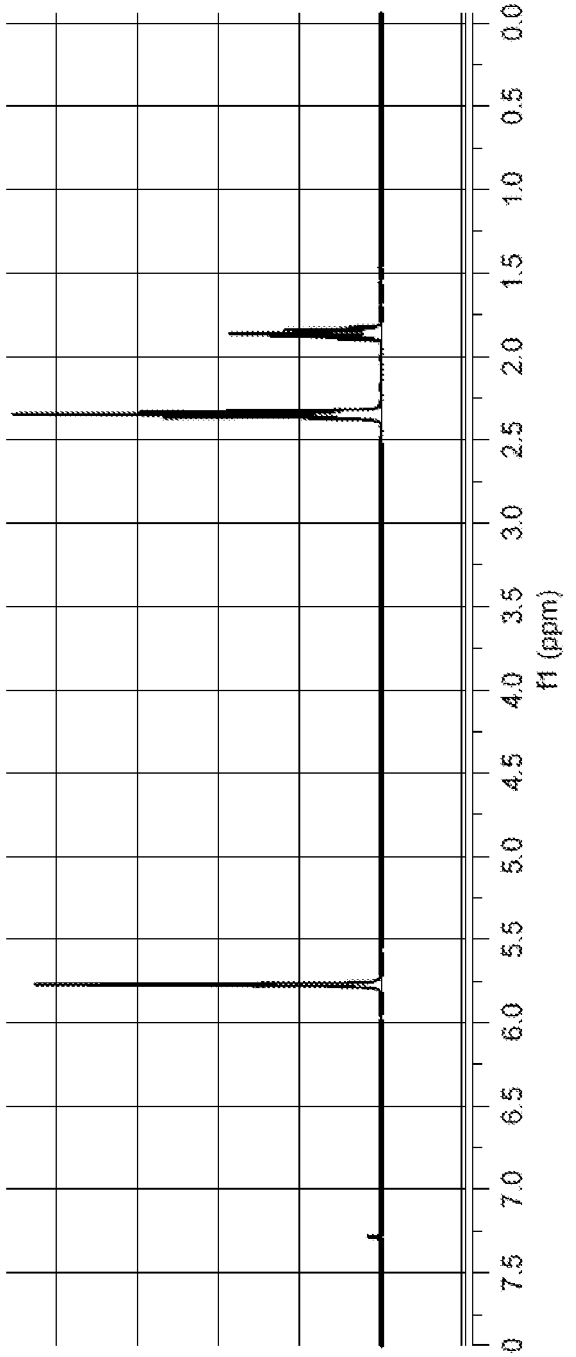
FIG. 2 is a $^1H$ NMR spectrum for recycled cyclopentene (in $CDCl_3$ solvent), according to an embodiment.

Example 12. Grubbs catalyst ($2^{nd}$ generation) was used (also referred to as benzylidene[1,3-bis(2,4,6-trimethylphenyl)-2-imidazolidinylidene]dichloro(tricyclohexylphosphine) ruthenium). Solid Grubbs catalyst ($2^{nd}$ generation, 30 mg, 0.05 mol %) was added to solid cured polypentenamer (Example 8, 5.0 g) in a 100 mL flask. The resulting mixture was stirred at 55-85° C. under vacuum in a completely closed system cooled by a liquid nitrogen compartment for collecting volatile depolymerization products. After 4 hours, the depolymerization reaction was visually completed yielding ca 4.65 g of a colorless liquid containing pure cyclopentene. The recycled monomer is pure according to $^1$H NMR spectroscopy (FIG. 2) and does not contain any traces of saturated cyclics or linear alpha olefins at an $^1$H NMR noticeable level. Recovery yield: 93%.

Example 13. Cured polypentenamer (4.62 g, Example 9) and Hoveyda-Grubbs catalyst ($2^{nd}$ Generation, 30 mg) were combined in 100 mL flask equipped with magnetic stirring and an outlet for removal and subsequent condensation of volatile depolymerization products. Depolymerization under stirring (60-200 rmp) in vacuo at 70-80° C. did not give a liquid product. Solid Grubbs catalyst ($2^{nd}$ generation, 30 mg) was then added and temperature was elevated to 90° C. Colorless liquid (0.7 g) was collected in 2 hours. The resulting recycled monomer consists of pure cyclopentene according to $^1$H NMR spectroscopy. Recovery yield: 25.4%.

Example 14. Cured polypentenamer (4.40 g, Example 10, cryogrinded), solid Grubbs catalyst ($2^{nd}$ Generation, 30 mg) and SpectraSyn4 (4 mL) were combined in 100 mL flask equipped with magnetic stirring and an outlet for removal and subsequent condensation of volatile depolymerization products. Depolymerization under stirring (60-200 rmp) in vacuo at 80° C. gave 0.68 g of colorless liquid in 2 hours. Further depolymerization for the remaining mixture was induced upon addition of toluene (ca 11 mL) and Hoveyda-Grubbs catalyst ($2^{nd}$ generation, 30 mg) and afforded in 2 hours at 80° C. a colorless solution (10.6 g) containing 0.41 g of cyclopentene in toluene according to $^1$H NMR spectroscopy. Overall recovery yield: 1.09 g (59.2%). The GC composition of both fractions are summarized in Table 9.

TABLE 9

| GC composition for the products obtained in Example 14. | | |
|---|---|---|
| | Area % | |
| Component | Fraction 1 | Fraction 2 |
| 3-Methyl-1-butene | 0.01396 | 0.01029 |
| 1-Pentene | 0.00599 | 0 |
| Cyclopentadiene | 0.00988 | 0 |
| Cyclopentene | 97.87501 | 3.66617 |
| Cyclopentane | 0.00198 | 0 |
| 1,5-Hexadiene | 0.04699 | 0.00159 |
| Benzene | 0.00291 | 0.00101 |
| Cyclohexadiene/Methylcyclopentadiene | 0.01498 | 0.0026 |
| Heptadiene | 0.00761 | 0 |
| Cyclohexene | 0.06491 | 0.00364 |
| Methyl Isobutyl Ketone | 0.00809 | 0 |
| Cyclopentane Oxide | 0.02702 | 0 |
| $C_5H_8O$ | 0.20602 | 0.0013 |
| Toluene | 0.70524 | 96.16644 |
| 4-Vinyl-Cyclohexene | 0.16674 | 0.00518 |
| Methylbenzene | 0.00369 | 0.038 |
| Meta- and para-Xylenes | 0.00264 | 0.02628 |
| Dicyclopentadiene | 0.00342 | 0 |
| $C_{10}H_{14}$ | 0.02752 | 0 |
| $C_{10}H_{14}$ | 0.02697 | 0 |
| unidentified products | 0.77843 | 0.0775 |

Example 15. Cured polypentenamer (10.3 g, Example 11, cryogrinded), solid Hoveyda-Grubbs catalyst ($2^{nd}$ generation, 40 mg) and SpectraSyn4 (20 mL) were combined in 100 mL flask equipped with magnetic stirring and an outlet for removal and subsequent condensation of volatile depolymerization products. Depolymerization under stirring (60-200 rmp) in vacuo at 75° C. gave 1.64 g of colorless liquid in 4 hours consisting of pure cyclopentene according to $^1$H NMR spectroscopy. The composition, estimated by GC is summarized in Table 10. Recovery yield: 87%.

TABLE 10

| GC composition for the products obtained in Example 15. | |
|---|---|
| Component | Area % |
| 3-Methyl-1-butene | 0.00926 |
| iso-Pentane | 0.02697 |
| 1-Pentene | 0.00374 |
| n-Pentane | 0.02849 |
| Cyclopentadiene | 0.01260 |
| Cyclopentene | 96.72487 |
| iso-Hexane | 0.04181 |
| iso-Hexane | 0.02915 |
| n-Hexane | 0.04094 |
| Cyclohexane | 0.17097 |
| Cyclohexadiene/Methylcyclopentadiene | 0.02413 |
| Heptadiene/iso-pentane | 0.05832 |
| Cyclohexene | 0.05591 |
| n-Heptane | 0.06358 |
| Methyl isobutyl ketone | 0.00659 |
| Toluene | 0.08209 |
| n-Octane | 0.08100 |
| 4-Vinyl-cyclohexene | 0.01207 |
| Meta- and para-Xylenes | 0.00383 |
| n-Nonane | 0.12899 |
| Dicyclopentadiene/n-decane | 0.84375 |
| $C_{10}H_{14}$ | 0.00477 |
| n-Undecane | 0.06749 |
| n-Dodecane | 0.05846 |
| n-Tridecane | 0.00735 |
| Unidentified products | 1.40893 |

TABLE 11

Summary of Depolymerization Experiments for Cured and Blended Polypentenamers.

| | Monomer recovery, mol % | Temperature, ° C. | Catalyst | Catalyst activity, g-cyclic olefin/g-Ru | Catalyst activity, g-cyclic olefin/g-Ru/hour |
|---|---|---|---|---|---|
| Example 12 | 93 | 55-85 | Grubbs ($2^{nd}$ generation) | 1303 | 326 |
| Example 13 | 25.5 | 70-90 | Hoveyda-Grubbs catalyst ($2^{nd}$ Generation) + Grubbs ($2^{nd}$ generation) | 83 | 42 |
| Example 14 | 59.2 | 80 | Hoveyda-Grubbs catalyst ($2^{nd}$ Generation) + Grubbs ($2^{nd}$ generation) | 130 | 32 |
| Example 15 | 87 | 75 | Hoveyda-Grubbs catalyst ($2^{nd}$ Generation) | 345 | 86 |

Overall, processes of the present disclosure can include treating a polymer (such as a polypentenamer or polyoctenamer) with a ring closing metathesis (RCM) catalyst to provide high yields of cyclic olefins (such as cyclopentene or cyclooctene). The high yield also provides high purity of the cyclic olefins. It has been discovered that high yields of cyclic olefins may be obtained without the use of added diluent (e.g., solvent) for the depolymerization, which improves the cost and throughput of an industrial scale depolymerization process. It has been further discovered that high yields of cyclic olefins may be obtained when treating vulcanized rubber (such as tires), for example with little or no pretreatment of the vulcanized rubber. Therefore, recycled cyclic olefins can be obtained in high yield (and high purity) for repurposing as starting monomers for polymerizations. The high purity of the recycled cyclic olefins can provide high purity recycled polymers (and vulcanized products thereof).

RE-POLYMERIZATION OF RECYCLED MONOMERS Highly active Ru-based catalysts for the ROMP of cyclopentene typically cannot produce the polymers, polypentenamers, with high molecular weights (>300 kDa) because of the presence of non-cyclic olefins that act as chain-transfer agents even at <1 mol %. It limits the application of Ru-based catalysts for the production of high Mw polypentenamers, suitable for the tire industry.

Commercial cyclopentene contains significant amounts of straight olefins that limits the number of available ROMP catalysts suitable for the production high molecular weight polypentenamers. The purification of cyclopentene from linear olefins by fractional distillation results in the significant loss of cyclopentene. Side products of manufacturing cyclopentene by selective hydrogenation of cyclopentadiene, 1,3-pentadienes (cis/trans), have a boiling points (42° C.) close to that in cyclopentene (44° C.). It makes the separation of cyclopentene from these disadvantageous contaminations challenging even at the industrial scale.

The purity of reclaimed cyclopentene is sufficient for re-polymerizing into high Mw polypentenamers. In terms of circularity it opens the opportunity to use the scrap polypentenamer-based tires for the production of renewable cyclopentene and subsequent re-polymerizing into high Mw polypentenamers using highly active Ru-cats.

In examples that follow, recycled cyclopentene, produced by depolymerization of polypentenamers (as discussed above), were used for the synthesis of high Mw polypentenamers (>400 kDa) using Grubbs catalyst or a Ziegler-Natta catalyst. Moreover, the polymerization of the recycled olefin can be performed with any of the catalysts discussed herein. The higher quality of the recycled cyclopentene vs. commercial monomer enables the synthesis of high Mw polymers, suitable for the tire industry.

Example 16. ROMP for Recycled Cyclopentene Using Ru-catalyst. The solution of Grubbs catalyst (dichloro[1,3-bis(2,6-isopropylphenyl)-2-imidazolidinylidene](benzylidene)(tricyclohexylphosphine)ruthenium(II), 7 mg, 0.0073 mmol) in toluene was added to neat recycled cyclopentene (50 g, 0.735 mol) at −35° C. The reaction mixture was allowed to warm up to 0° C. over 30 minutes before adding 300 mL of dichloromethane containing ethyl vinyl ether (0.5 mL). The resulting mixture was stirred for 12 hours at ambient conditions until all polymer product was dissolved. The product was precipitated with methanol containing 2,6-di-tert-butyl-4-methylphenol (0.5 g) and dried in vacuo at 55° C. to give polypentenamer in the yield of up to 94% (Table 11).

Example 17. ROMP for Commercial Cyclopentene Using Ru-catalyst. The solution of Grubbs catalyst (dichloro[1,3-bis(2,6-isopropylphenyl)-2-imidazolidinylidene](benzylidene)(tricyclohexylphosphine)ruthenium(II), 7 mg, 0.0073 mmol) in toluene was added to neat commercial cyclopentene (50 g, 0.735 mol) at −35° C. The reaction mixture was allowed to warm up to 0° C. over 30 minutes before adding 300 mL of dichloromethane containing ethyl vinyl ether (0.5 mL). The resulting mixture was stirred for 12 hours at ambient conditions until all polymer product was dissolved. The product was precipitated with methanol containing 2,6-di-tert-butyl-4-methylphenol (0.5 g) and dried in vacuo at 55° C. to give polypentenamer in the yield of 74% (Table 11).

TABLE 11

Data for Polypentenamers Produced Using Recycled or Commercial Cyclopentene and Ru-catalyst.

| Exp # | Ru:monomer | m prepared, g | Yield, % | Mw, kDa | PDI | Cat efficiency, $kg_{product}/g_{cat}$ |
|---|---|---|---|---|---|---|
| Example 16; run 1 | 1:10 000 | 47 | 94 | 539 | 1.69 | 6.7 |
| Example 16; run 2 | 1:10 000 | 54 | 90 | 471 | 1.72 | 6.0 |
| Example 16, run 3 | 1:10 000 | 37 | 93 | 476 | 1.82 | 6.5 |
| Example 17 | 1:10 000 | 26 | 74 | 72 | 1.83 | 5.2 |

Example 18. ROMP for Recycled Cyclopentene Using Ziegler-Natta Catalyst. The catalyst was formed in situ by adding solid $(p\text{-}MeC_6H_4O)_2AlCl$ (102 mg, 0.368 mmol) to a solution of $WCl_6$ (73 mg, 0.184 mmol) in toluene (5 mL). After stirring for one hour, the resulting mixture was added to the solution of cyclopentene (50.2 g, 738 mol) and triethylaluminum (42.1 mg, 0.369 mmol) in toluene (600 mL) at 0° C. After 180 minutes of intense mechanical stirring, a solution of 2,6-di-tert-butyl-4-methylphenol (1.00 g, 4.48 mmol) in 100 mL of ethanol/toluene mixture (1:4, v:v, respectively) was added. The obtained mixture was poured into ethanol (1 L). The precipitated polymer was then washed 3 times with ethanol (ca 100 mL each) and dried under vacuum at 50° C. for 4 hours to give 23.0 g of the polymeric product.

Example 19. ROMP for Commercial Cyclopentene Using Ziegler-Natta Catalyst. The catalyst was formed in situ by adding solid $(p\text{-}MeC_6H_4O)_2AlCl$ (202 mg, 0.731 mmol) to a solution of $WCl_6$ (145 mg, 0.366 mmol) in toluene (10 mL). After stirring for one hour, the resulting mixture was added to the solution of cyclopentene (99.7 g, 1.464 mol) and triethylaluminum (84 mg, 0.732 mmol) in toluene (500 mL) at 0° C. After 60 minutes of intense mechanical stirring, a solution of 2,6-di-tert-butyl-4-methylphenol (1.00 g, 4.48 mmol) in 100 mL of ethanol/toluene mixture (1:4, v:v, respectively) was added. The obtained mixture was poured into ethanol (2 L). The precipitated polymer was then washed 3 times with ethanol (250 mL each) and dried under vacuum at 50° C. for 4 hours to give 43.0 g of the polymeric product.

TABLE 12

Data for Polypentenamers Produced Using Recycled or Commercial Cyclopentene and Ziegler-Natta Catalyst.

| Exp # | W:monomer | m prepared, g | Yield, % | Mw, kDa | PDI | Cat efficiency, $kg_{product}/g_W$ |
|---|---|---|---|---|---|---|
| Example 18 | 1:4000 | 23.0 | 46 | 379 | 1.89 | 0.68 |
| Example 19 | 1:4000 | 43 | 43 | 312 | 2.06 | 0.64 |

In at least one embodiment, the reactants (for example, metathesis catalyst; recycled olefin, optional diluent, etc.) are combined in a reaction vessel at a temperature of at a temperature of from less than 30° C. to −60° C., preferably at a temperature of from −10° C. to −50° C., such as from −20° C. up to −40° C., or less than −10° C., −20° C. or −30° C., so that the internal temperature of the reactor is maintained in a desired range, e.g., within 1° C., −15° C., −25° C., −35° C. and/or at a pressure of about 1 atmosphere, and/or for a residence time of 0.5 seconds to 48 hours (such as 0.25 seconds to 5 hours, such as 30 minutes to 2 hours).

In at least one embodiment of polymerization of a recycled olefin using ROMP reaction, the catalyst is present at from 0.001 nanomoles of transition metal per mole of unsaturated polymer to 1 millimole of transition metal per mole of unsaturated polymer, based upon the moles of unsaturated polymer feed into the reactor. Alternately, the catalyst is present at from 0.01 nanomoles of transition metal per mole of unsaturated polymer to 0.1 millimole of transition metal per mole of unsaturated polymer, alternately from 0.1 nanomoles of transition metal unsaturated polymer to 0.075 millimole of transition metal per mole of unsaturated polymer, based upon the moles of unsaturated polymer feed into the reactor.

Processes of the present disclosure can be batch, semi-batch or continuous. As used herein, the term continuous means a system that operates without interruption or cessation. For example, a continuous process to produce polymers from recycled cyclic olefins would be one where the reactants are continually introduced into one or more reactors and polymer product is continually withdrawn.

The processes for polymerization of recycled olefins may be conducted in any suitable reaction vessel, such as glass lined, stainless steel, or similar type reaction equipment. Useful reaction vessels include reactors (including continuous stirred tank reactors, batch reactors, reactive extruder, pipe, or pump, continuous flow fixed bed reactors, slurry reactors, fluidized bed reactors, and catalytic distillation reactors). The reaction zone may be fitted with one or more internal and/or external heat exchanger(s) in order to control undue temperature fluctuations, or to prevent "runaway" reaction temperatures.

The quantity of catalyst that is employed in a polymerization of recycled olefins is any quantity that provides for an operable metathesis reaction. The ratio of moles of monomer units of a polymer (of the polymer starting material) to moles of catalyst can be typically greater than about 10:1, such as greater than about 100:1, such as greater than about 1000:1, such as greater than about 10,000:1, such as greater than about 25,000:1, such as greater than about 50,000:1, such as greater than about 100,000:1. Alternately, the molar ratio of monomer units of a polymer to catalyst is less than about 10,000,000:1, such as less than about 1,000,000:1, such as less than about 500,000:1.

The contacting time of the reagents and catalyst in a batch reactor can be any duration, provided that the polymer products are obtained. Generally, the contacting time in a reactor is greater than about 5 minutes, such as greater than about 10 minutes. Generally, the to contacting time in a reactor is less than about 25 hours, such as less than about 15 hours, such as less than about 10 hours.

The phrases, unless otherwise specified, "consists essentially of" and "consisting essentially of" do not exclude the presence of other steps, elements, or materials, whether or not, specifically mentioned in this specification, so long as such steps, elements, or materials, do not affect the basic and novel characteristics of the present disclosure, additionally, they do not exclude impurities and variances normally associated with the elements and materials used.

For the sake of brevity, only certain ranges are explicitly disclosed herein. However, ranges from any lower limit may be combined with any upper limit to recite a range not explicitly recited, as well as, ranges from any lower limit may be combined with any other lower limit to recite a range not explicitly recited, in the same way, ranges from any upper limit may be combined with any other upper limit to recite a range not explicitly recited. Additionally, within a range includes every point or individual value between its end points even though not explicitly recited. Thus, every point or individual value may serve as its own lower or upper limit combined with any other point or individual value or any other lower or upper limit, to recite a range not explicitly recited.

All documents described herein are incorporated by reference herein, including any priority documents and or testing procedures to the extent they are not inconsistent with this text. As is apparent from the foregoing general description and the specific embodiments, while forms of the present disclosure have been illustrated and described, various modifications can be made without departing from the spirit and scope of the present disclosure. Accordingly, it is not intended that the present disclosure be limited thereby. Likewise, the term "comprising" is considered synonymous with the term "including" for purposes of United States law. Likewise whenever a composition, an element or a group of elements is preceded with the transitional phrase "comprising," it is understood that we also contemplate the same composition or group of elements with transitional phrases "consisting essentially of," "consisting of," "selected from the group of consisting of," or "is" preceding the recitation of the composition, element, or elements and vice versa.

While the present disclosure has been described with respect to a number of embodiments and examples, those skilled in the art, having benefit of this disclosure, will appreciate that other embodiments can be devised which do not depart from the scope and spirit of the present disclosure.

We claim:

1. A process for producing a volatile cyclic monoolefin, the process comprising:

introducing an unsaturated polymer comprising a vulcanized polymer to a metathesis catalyst in a reaction vessel under reaction conditions, wherein the vulcanized polymer further comprises a copolymer of polypentenamer and polyoctenamer; and obtaining a product comprising the volatile cyclic monoolefin.

2. The process of claim 1, wherein the copolymer of polypentenamer and polyoctenamer is represented by Formula (IV):

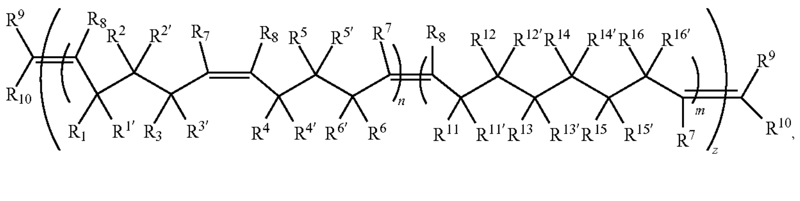

(IV)

wherein:

n is an integer from 1 to about 25,000;

m is an integer from 1 to about 25,000;

z is an integer from 1 to about 5,000;

each of $R^1$, $R^{1'}$, $R^2$, $R^{2'}$, $R^3$, $R^{3'}$, $R^4$, $R^{4'}$, $R^5$, $R^{5'}$, $R^6$, $R^{6'}$, $R^7$, $R^8$, $R^{11}$, $R^{11'}$, $R^{12}$, $R^{12'}$, $R^{13}$, $R^{13'}$ $R^{14}$, $R^{14'}$, $R^{15}$, $R^{15'}$, $R^{16}$, and $R^{16'}$ is independently hydrogen, $C_1$-$C_{40}$ hydrocarbyl, or $R^1$ and $R^2$, $R^1$ and $R^3$, $R^2$ and $R^3$, $R^4$ and $R^5$, $R^5$ and $R^6$, $R^{11}$ and $R^{12}$, $R^{12}$ and $R^{13}$, $R^{13}$ and $R^{14}$, $R^{14}$ and $R^{15}$, or $R^{15}$ and $R^{16}$ join together to form a saturated or unsaturated cyclic $C_5$-$C_{10}$ hydrocarbyl; and each $R^9$ and $R^{10}$ is independently hydrogen or an end cap, wherein the end cap is an ether, an amine, an aryl, or a carboxylic acid.

3. The process of claim 2, wherein:

n is from about 500 to about 5,000;

m is from about 500 to about 5,000;

z is from about 100 to about 3,000;

each of $R^1$, $R^{1'}$, $R^2$, $R^{2'}$, $R^3$, $R^{3'}$, $R^4$, $R^{4'}$, $R^5$, $R^{5'}$, $R^6$, $R^{6'}$, $R^7$, $R^8$, $R^{11}$, $R^{11'}$, $R^{12}$, $R^{12'}$, $R^{13}$, R 13' $R^{14}$, $R^{14'}$, $R^{15}$, $R^{15'}$, $R^{16}$, and $R^{16'}$ is independently hydrogen or $C_1$-$C_{10}$ hydrocarbyl; and each $R^9$ and $R^{10}$ is independently the end cap, the end cap is the ether selected from the group consisting of ethyl ether, propyl ether, butyl ether, pentyl ether, and hexyl ether.

4. The process of claim 1, wherein the copolymer of polypentenamer and polyoctenamer is represented by Formula (V):

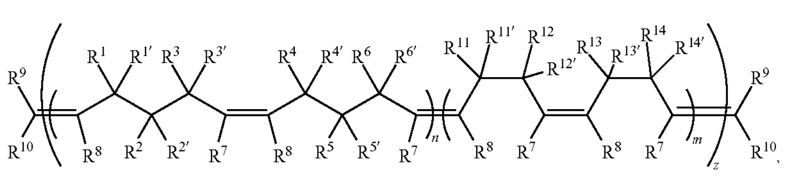

(V)

wherein:

n is an integer from 1 to about 25,000;

m is an integer from 1 to about 25,000;

z is an integer from 1 to about 5,000;

each of $R^1$, $R^{1'}$, $R^2$, $R^{2'}$, $R^3$, $R^{3'}$, $R^4$, $R^{4'}$, $R^5$, $R^{5'}$, $R^6$, $R^{6'}$, $R^7$, $R^8$, $R^{11}$, $R^{11'}$, $R^{12}$, $R^{12'}$, $R^{13}$, $R^{13'}$, $R^{14}$, and $R^{14'}$ is independently hydrogen, $C_1$-$C_{40}$ hydrocarbyl, or $R^1$ and $R^2$, $R^1$ and $R^3$, $R^2$ and $R^3$, $R^4$ and $R^5$, $R^5$ and $R^6$, $R^{11}$ and $R^{12}$, or $R^{13}$ and $R^{14}$, join together to form a saturated or unsaturated cyclic $C_5$-$C_{10}$ hydrocarbyl; and each $R^9$ and $R^{10}$ is independently hydrogen or an end cap, wherein the end cap is an ether, an amine, an aryl, or a carboxylic acid.

5. The process of claim 4, wherein:

n is from about 500 to about 5,000;

m is from about 500 to about 5,000;

z is from about 100 to about 3,000;

each of $R^1$, $R^{1'}$, $R^2$, $R^{2'}$, $R^3$, $R^{3'}$, $R^4$, $R^{4'}$, $R^5$, $R^{5'}$, $R^6$, $R^{6'}$, $R^7$, $R^8$, $R^{11}$, $R^{11'}$, $R^{12}$, $R^{12'}$, $R^{13}$, $R^{13'}$, $R^{14}$, and $R^{14'}$ is independently hydrogen or $C_1$-$C_{10}$ hydrocarbyl; and each $R^9$ and $R^{10}$ is independently the end cap, the end cap is the ether selected from the group consisting of ethyl ether, propyl ether, butyl ether, pentyl ether, and hexyl ether.

6. A process comprising:

introducing a volatile cyclic monoolefin, chemically recycled from an unsaturated polymer comprising a vulcanized polymer, to a metathesis catalyst in a reaction vessel under polymerization reaction conditions and producing a product that includes a high molecular weight polymer, wherein the vulcanized polymer further comprises a copolymer of polypentenamer and polyoctenamer.

7. The process of claim 6, wherein the copolymer of polypentenamer and polyoctenamer is represented by Formula (IV):

(IV)

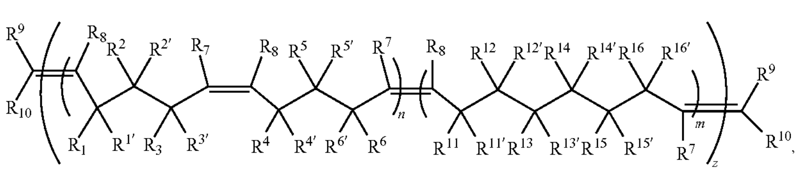

wherein:

n is an integer from 1 to about 25,000;

m is an integer from 1 to about 25,000;

z is an integer from 1 to about 5,000;

each of $R^1$, $R^{1'}$, $R^2$, $R^{2'}$, $R^3$, $R^{3'}$, $R^4$, $R^{4'}$, $R^5$, $R^{5'}$, $R^6$, $R^{6'}$, $R^7$, $R^8$, $R^{11}$, $R^{11'}$, $R^{12}$, $R^{12'}$, $R^{13}$, $R^{13'}$, $R^{14}$, $R^{14'}$, $R^{15}$, $R^{15'}$, $R^{16}$, and $R^{16'}$ is independently hydrogen, $C_1$-$C_{40}$ hydrocarbyl, or $R^1$ and $R^2$, $R^1$ and $R^3$, $R^2$ and $R^3$, $R^4$ and $R^5$, $R^5$ and $R^6$, $R^{11}$ and $R^{12}$, $R^{12}$ and $R^{13}$, $R^{13}$ and $R^{14}$, $R^{14}$ and $R^{15}$, or $R^{15}$ and $R^{16}$ join together to form a saturated or unsaturated cyclic $C_5$-$C_{10}$ hydrocarbyl; and each $R^9$ and $R^{10}$ is independently hydrogen or an end cap, wherein the end cap is an ether, an amine, an aryl, or a carboxylic acid.

8. The process of claim 7, wherein:

n is from about 500 to about 5,000;

m is from about 500 to about 5,000;

z is from about 100 to about 3,000;

each of $R^1$, $R^{1'}$, $R^2$, $R^{2'}$, $R^3$, $R^{3'}$, $R^4$, $R^{4'}$, $R^5$, $R^{5'}$, $R^6$, $R^{6'}$, $R^7$, $R^8$, $R^{11}$, $R^{11'}$, $R^{12}$, $R^{12'}$, $R^{13}$, $R^{13'}$, $R^{14}$, $R^{14'}$, $R^{15}$, $R^{15'}$, $R^{16}$, and $R^{16'}$ is independently hydrogen or $C_1$-$C_{10}$ hydrocarbyl; and each $R^9$ and $R^{10}$ is independently the end cap, and the end cap is the ether selected from the group consisting of ethyl ether, propyl ether, butyl ether, pentyl ether, and hexyl ether.

9. The process of claim 6, wherein the copolymer of polypentenamer and polyoctenamer is represented by Formula (V):

(V)

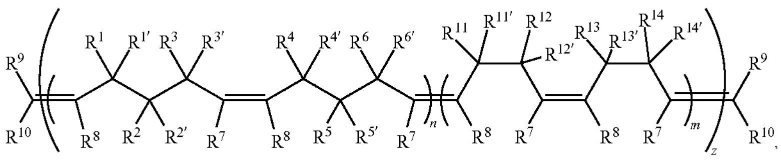

wherein:

n is an integer from 1 to about 25,000;

m is an integer from 1 to about 25,000;

z is an integer from 1 to about 5,000;

each of $R^1$, $R^{1'}$, $R^2$, $R^{2'}$, $R^3$, $R^{3'}$, $R^4$, $R^{4'}$, $R^5$, $R^{5'}$, $R^6$, $R^{6'}$, $R^7$, $R^8$, $R^{11}$, $R^{11'}$, $R^{12}$, $R^{12'}$, $R^{13}$, $R^{13'}$, $R^{14}$, and $R^{14'}$ is independently hydrogen, $C_1$-$C_{40}$ hydrocarbyl, or $R^1$ and $R^2$, $R^1$ and $R^3$, $R^2$ and $R^3$, $R^4$ and $R^5$, $R^5$ and $R^6$, $R^{11}$ and $R^{12}$, or $R^{13}$ and $R^{14}$, join together to form a saturated or unsaturated cyclic $C_5$-$C_{10}$ hydrocarbyl; and each $R^9$ and $R^{10}$ is independently hydrogen or an end cap, wherein the end cap is an ether, an amine, an aryl, or a carboxylic acid.

10. The process of claim 9, wherein:

n is from about 500 to about 5,000;

m is from about 500 to about 5,000;

z is from about 100 to about 3,000;

each of $R^1$, $R^{1'}$, $R^2$, $R^{2'}$, $R^3$, $R^{3'}$, $R^4$, $R^{4'}$, $R^5$, $R^{5'}$, $R^6$, $R^{6'}$, $R^7$, $R^8$, $R^{11}$, $R^{11'}$, $R^{12}$, $R^{12'}$, $R^{13}$, $R^{13'}$, $R^{14}$, and $R^{14'}$ is independently hydrogen or $C_1$-$C_{10}$ hydrocarbyl; and each $R^9$ and $R^{10}$ is independently the end cap, and the end cap is the ether selected from the group consisting of ethyl ether, propyl ether, butyl ether, pentyl ether, and hexyl ether.

* * * * *